(12) United States Patent
Ikeda et al.

(10) Patent No.: US 7,790,892 B2
(45) Date of Patent: Sep. 7, 2010

(54) AROMATIC COMPOUND AND ORGANIC ELECTROLUMINESCENT ELEMENT CONTAINING THE SAME

(75) Inventors: Hidetsugu Ikeda, Sodegaura (JP); Masahide Matsuura, Sodegaura (JP); Masakazu Funahashi, Sodegaura (JP); Chishio Hosokawa, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 112 days.

(21) Appl. No.: 10/508,602

(22) PCT Filed: Apr. 17, 2003

(86) PCT No.: PCT/JP03/04905

§ 371 (c)(1), (2), (4) Date: Mar. 16, 2005

(87) PCT Pub. No.: WO03/087023

PCT Pub. Date: Oct. 23, 2003

(65) Prior Publication Data

US 2005/0214565 A1    Sep. 29, 2005

(30) Foreign Application Priority Data

Apr. 17, 2002  (JP) ............................ 2002-114400

(51) Int. Cl.
*H01J 1/62* (2006.01)
*C09K 11/06* (2006.01)
*C07D 215/00* (2006.01)
*C07D 215/44* (2006.01)
*C07D 213/72* (2006.01)
*C07D 209/82* (2006.01)

(52) U.S. Cl. ........................ 546/152; 546/159; 546/304; 428/690; 428/917; 252/301.16; 548/440

(58) Field of Classification Search ................. 428/690, 428/917; 313/504, 506; 252/301.16; 257/40, 257/90, 89
See application file for complete search history.

(56) References Cited

U.S. PATENT DOCUMENTS

| | | | |
|---|---|---|---|
| 593,571 A | 11/1897 | Fay | |
| 6,929,870 B2 * | 8/2005 | Ishida et al. | 428/690 |
| 2002/0048688 A1 * | 4/2002 | Fukuoka et al. | 428/690 |
| 2003/0087126 A1 * | 5/2003 | Ishida et al. | 428/690 |

FOREIGN PATENT DOCUMENTS

| | | |
|---|---|---|
| EP | 0 681 019 A2 | 11/1995 |
| EP | 1 182 183 A1 | 2/2002 |
| EP | 1 191 822 A1 | 3/2002 |
| EP | 1 221 434 A1 | 7/2002 |
| EP | 1 440 959 | 7/2004 |
| JP | 03-200889 | 9/1991 |
| JP | 07-138561 | 5/1995 |
| JP | 08-012600 | 1/1996 |
| JP | 08-239655 | 9/1996 |
| JP | 11-329732 | 11/1999 |
| JP | 2000-273056 | 10/2000 |
| JP | 2001-097897 | 4/2001 |

* cited by examiner

*Primary Examiner*—D. Lawrence Tarazano
*Assistant Examiner*—Camie S Thompson
(74) *Attorney, Agent, or Firm*—Steptoe & Johnson LLP

(57) ABSTRACT

A novel aromatic compound having an anthracene skeleton structure and an asymmetric molecular structure; and an organic electroluminescence device which comprises a cathode, an anode and an organic thin film layer comprising at least one layer containing a light emitting layer and sandwiched between the cathode and the anode in which at least one layer in the organic thin film layer contains the above novel aromatic compound singly or as a component of a mixture. The organic electroluminescence device exhibits a great luminance of emitted light, a great efficiency of light emission and a high purity of color, emits bluish light, is excellent in stability at high temperatures and has a long life. The organic electroluminescence device can be provided by utilizing the novel aromatic compound.

11 Claims, No Drawings

AROMATIC COMPOUND AND ORGANIC ELECTROLUMINESCENT ELEMENT CONTAINING THE SAME

TECHNICAL FIELD

The present invention relates to a novel aromatic compound and an organic electroluminescent ("electroluminescent" and "electro-luminescence" will be referred to as "EL", hereinafter) device containing the compound and, more particularly, to a novel aromatic compound which can provide an organic EL device exhibiting a great luminance of emitted light, a great efficiency of light emission and a high purity of color, emitting bluish light, excellent in stability at high temperatures and having a long life and an organic EL device utilizing the compound.

BACKGROUND ART

An organic EL device is a spontaneous light emitting device which utilizes the principle that a fluorescent substance emits light by energy of recombination of holes injected from an anode and electrons injected from a cathode when an electric field is applied. Since an organic EL device of the laminate type driven under a low-electric voltage was reported by C. W. Tang of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-hydroxyquinolinol)aluminum for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed within the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

As the light emitting material, chelate complexes such as tris(8-quinolinolato)aluminum, coumarine derivatives, tetraphenyl-butadiene derivatives, bisstyrylarylene derivatives and oxadiazole derivatives are known. It is reported that light in the visible region ranging from blue light to red light can be obtained by using these light emitting materials, and development of a device exhibiting color images is expected (For example, Japanese Patent Application Laid-Open Nos. Heisei 8(1996)-239655, Heisei 7(1995)-138561 and Heisei 3(1991)-200889).

A device using a phenylanthracene derivative as the light emitting material is disclosed in Japanese Patent Application Laid-Open No. Heisei 8(1996)-012600. Although the anthracene derivative is used as the material for emitting bluish light, a further improvement in the efficiency of light emission has been desired. On the other hand, an improvement in the stability of the thin film has been desired so that the life of the device is increased. However, heretofore known anthracene derivatives form crystals in many cases to cause fracture of the thin film, and the improvement has been desired. For example, a dinaphthylanthracene compound is disclosed in the U.S. Pat. No. 0,593,571. However, since this compound has a symmetric molecular structure in the horizontal and vertical directions, the molecules are easily arranged to form crystals during storage at high temperatures and driving at high temperatures. Japanese Patent Application Laid-Open No. Heisei 2000-273056 discloses an allylanthracene compound asymmetric in the horizontal direction. However, one of the groups as substituents to the anthracendiyl group is a simple group such as phenyl group and biphenyl group, and the crystallization cannot be prevented.

DISCLOSURE OF THE INVENTION

The present invention has been made to overcome the above problems and has an object of providing a novel aromatic compound which can provide an organic EL device exhibiting a great luminance of emitted light, a great efficiency of light emission and a high purity of color, emitting bluish light, excellent in stability at high temperatures and having a long life and an organic EL device utilizing the compound.

As the result of intensive studies by the present inventors to overcome the above problems, it was found that the above problems could be overcome by using a compound which has a high glass transition temperature and an asymmetric molecular structure as the material for the organic thin film layer of an organic EL device. The present invention has been completed based on this knowledge.

The present invention provides a novel aromatic compound represented by following general formula (A) or (B).

General formula (A) is:

$$A\text{-}Ar\text{—}B \qquad (A)$$

wherein Ar represents a substituted or unsubstituted anthracendiyl group, B represents a heterocyclic group which has 2 to 60 carbon atoms or a substituted or unsubstituted aryl group having 5 to 60 carbon atoms each of which is monosubstituted with an alkenyl group or an arylamino group, A represents a group which is selected from groups represented by the following general formulae (1) to (11):

-continued

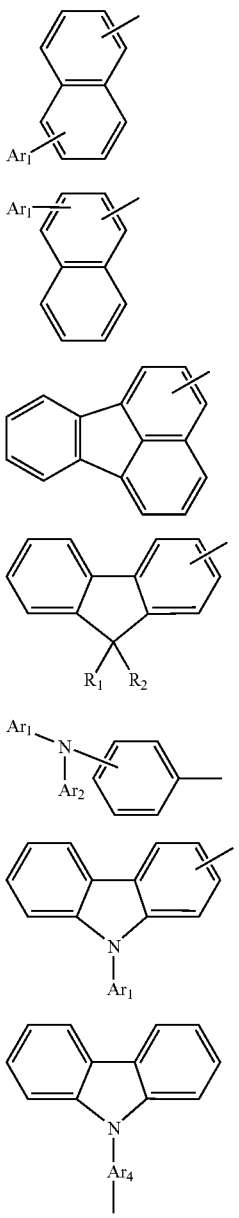

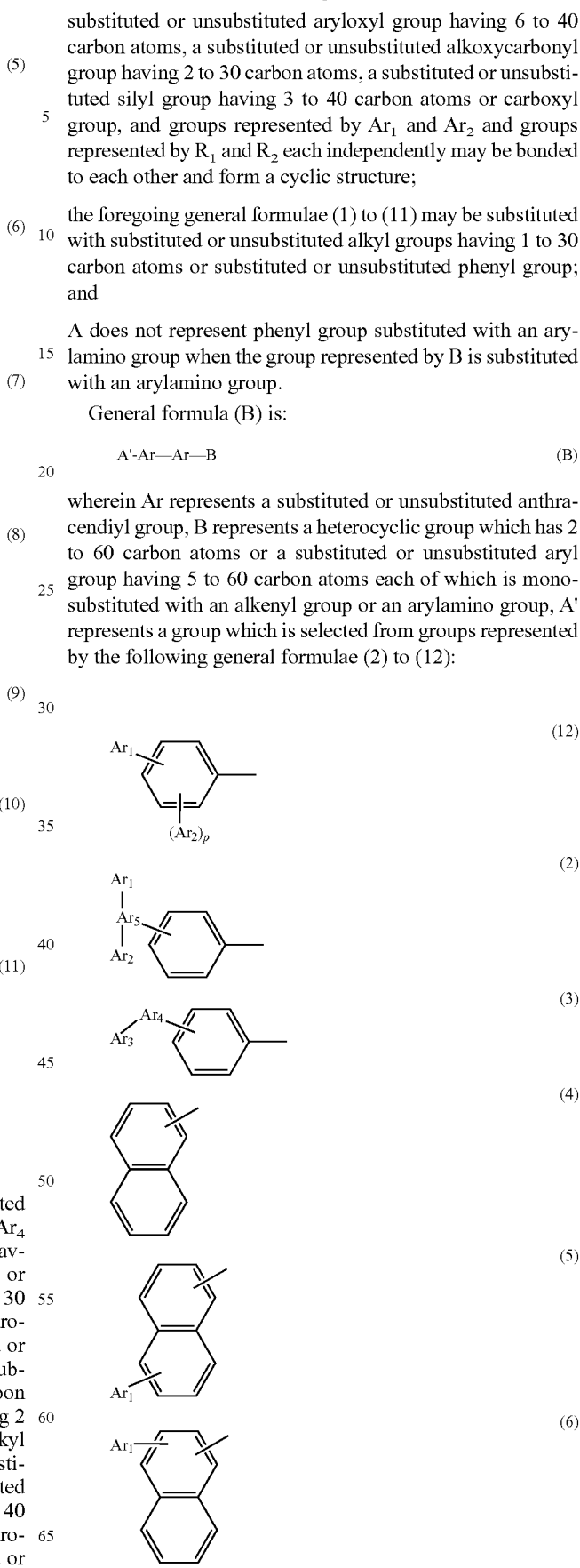

wherein $Ar_1$ to $Ar_3$ each independently represent a substituted or unsubstituted aryl group having 6 to 30 carbon atoms, $Ar_4$ represents a substituted or unsubstituted arylene group having 6 to 30 carbon atoms, $Ar_5$ represents a substituted or unsubstituted trivalent aromatic residue group having 6 to 30 carbon atoms, $R_1$ and $R_2$ each independently represent hydrogen atom, a halogen atom, hydroxyl group, a substituted or unsubstituted amino group, nitro group, cyano group, a substituted or unsubstituted alkyl group having 1 to 30 carbon atoms, a substituted or unsubstituted alkenyl group having 2 to 40 carbon atoms, a substituted or unsubstituted cycloalkyl group having 5 to 40 carbon atoms, a substituted or unsubstituted alkoxyl group having 1 to 30 carbon atoms, a substituted or unsubstituted aromatic hydrocarbon group having 5 to 40 carbon atoms, a substituted or unsubstituted aromatic heterocyclic group having 2 to 40 carbon atoms, a substituted or unsubstituted aralkyl group having 7 to 40 carbon atoms, a substituted or unsubstituted aryloxyl group having 6 to 40 carbon atoms, a substituted or unsubstituted alkoxycarbonyl group having 2 to 30 carbon atoms, a substituted or unsubstituted silyl group having 3 to 40 carbon atoms or carboxyl group, and groups represented by $Ar_1$ and $Ar_2$ and groups represented by $R_1$ and $R_2$ each independently may be bonded to each other and form a cyclic structure;

the foregoing general formulae (1) to (11) may be substituted with substituted or unsubstituted alkyl groups having 1 to 30 carbon atoms or substituted or unsubstituted phenyl group; and A does not represent phenyl group substituted with an arylamino group when the group represented by B is substituted with an arylamino group.

General formula (B) is:

$$A'\text{-}Ar\text{---}Ar\text{---}B \quad (B)$$

wherein Ar represents a substituted or unsubstituted anthracendiyl group, B represents a heterocyclic group which has 2 to 60 carbon atoms or a substituted or unsubstituted aryl group having 5 to 60 carbon atoms each of which is monosubstituted with an alkenyl group or an arylamino group, A' represents a group which is selected from groups represented by the following general formulae (2) to (12):

-continued

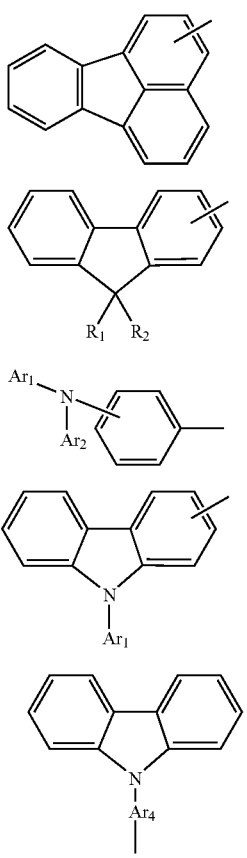

(7)

(8)

(9)

(10)

(11)

wherein Ar₁ to Ar₃ each independently represent a substituted or unsubstituted aryl group having 6 to 30 carbon atoms, Ar₄ represents a substituted or unsubstituted arylene group having 6 to 30 carbon atoms, Ar₅ represents a substituted or unsubstituted trivalent aromatic residue group having 6 to 30 carbon atoms, R₁ and R₂ each independently represent hydrogen atom, a halogen atom, hydroxyl group, a substituted or unsubstituted amino group, nitro group, cyano group, a substituted or unsubstituted alkyl group having 1 to 30 carbon atoms, a substituted or unsubstituted alkenyl group having 2 to 40 carbon atoms, a substituted or unsubstituted cycloalkyl group having 5 to 40 carbon atoms, a substituted or unsubstituted alkoxyl group having 1 to 30 carbon atoms, a substituted or unsubstituted aromatic hydrocarbon group having 5 to 40 carbon atoms, a substituted or unsubstituted aromatic heterocyclic group having 2 to 40 carbon atoms, a substituted or unsubstituted aralkyl group having 7 to 40 carbon atoms, a substituted or unsubstituted aryloxyl group having 6 to 40 carbon atoms, a substituted or unsubstituted alkoxycarbonyl group having 2 to 30 carbon atoms, a substituted or unsubstituted silyl group having 3 to 40 carbon atoms or carboxyl group, groups represented by Ar₁ and Ar₂ and groups represented by R₁ and R₂ each independently may be bonded to each other and form a cyclic structure, and p in general formula (12) represents 0 or 1;

the foregoing general formulae (1) to (11) may be substituted with substituted or unsubstituted alkyl groups having 1 to 30 carbon atoms or substituted or unsubstituted phenyl group; and A does not represent phenyl group substituted with an arylamino group when the group represented by B is substituted with an arylamino group.

The present invention also provides an organic EL device which comprises a cathode, an anode and an organic thin film layer comprising at least one layer containing a light emitting layer and sandwiched between the cathode and the anode, wherein at least one layer in the organic thin film layer comprises a novel aromatic compound represented by general formula (A) or (B) singly or as a component of a mixture.

THE MOST PREFERRED EMBODIMENT TO CARRY OUT THE INVENTION

The present invention provides a novel compound represented by the following general formula (A) or (B):

A-Ar—B     (A)

A'-Ar—Ar—B     (B)

In the above general formulae (A) and (B), Ar represents a substituted or unsubstituted anthracendiyl group.

In the above general formulae (A) and (B), B represents a heterocyclic group which has 2 to 60 carbon atoms or a substituted or unsubstituted aryl group having 5 to 60 carbon atoms each of which is monosubstituted with an alkenyl group or an arylamino group. It is preferable that B represents a heterocyclic group which has 2 to 60 carbon atoms and is monosubstituted with an alkenyl group or an arylamino group or an aryl group which has 5 to 60 carbon atoms and is monosubstituted with an alkenyl group or an arylamino group.

Examples of the alkenyl group as the substituent in the group represented by B include vinyl group, allyl group, 1-butenyl group, 2-butenyl group, 3-butenyl group, 1,3-butadienyl group, 1-methylvinyl group, styryl group, 2,2-diphenylvinyl group, 2,2-ditolylvinyl group, 1,2-ditolylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl-1-butenyl group and 3-phenyl-1-butenyl group.

Examples of the arylamino group as the substituent in the group represented by B include phenylamino group, diphenylamino group, biphenylamino group, naphthylamino group, anthranylamino group, ditolylamino group, dinaphthylamino group, phenylnaphthylamino group, phenylmethylamino group, pyrenylphenylamino group, biphenylamino group and biphenylnaphthylamino group.

Examples of the substituted or unsubstituted heterocyclic group as the substituent in the group represented by B include 1-pyrrolyl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group. The above group has 2 to 60 carbon atoms including the above substituents.

Examples of the aryl group represented by B include phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxadiazolyl group, diphenylanthranyl group, indolyl group, carbazolyl group, pyridyl group, benzoquinolyl group, fluoranthenyl group and acenaphthofluoranthenyl group. The above group has 5 to 60 carbon atoms including the above substituents.

In the above general formula (A), A represents a group which is selected from groups represented by general formulae (1) to (11):

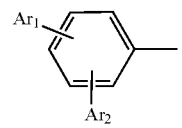 (1)

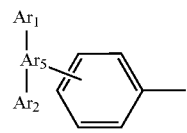 (2)

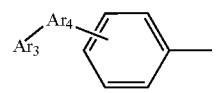 (3)

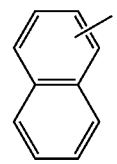 (4)

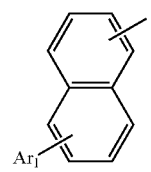 (5)

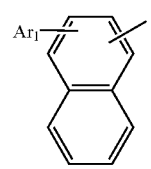 (6)

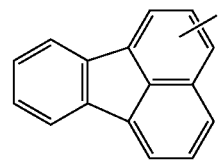 (7)

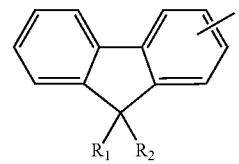 (8)

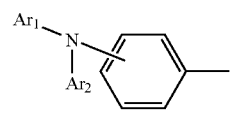 (9)

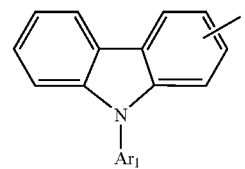 (10)

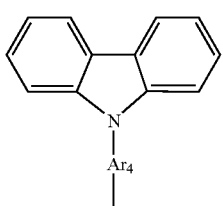

(11)

In general formulae (1) to (11), $Ar_1$ to $Ar_3$ each independently represent a substituted or unsubstituted aryl group having 6 to 30 carbon atoms, $Ar_4$ represents a substituted or unsubstituted arylene group having 6 to 30 carbon atoms, $Ar_5$ represents a substituted or unsubstituted trivalent aromatic residue group having 6 to 30 carbon atoms, and $R_1$ and $R_2$ each independently represent hydrogen atom, a halogen atom, hydroxyl group, a substituted or unsubstituted amino group, nitro group, cyano group, a substituted or unsubstituted alkyl group having 1 to 30 carbon atoms, a substituted or unsubstituted alkenyl group having 2 to 40 carbon atoms, a substituted or unsubstituted cycloalkyl group having 5 to 40 carbon atoms, a substituted or unsubstituted alkoxyl group having 1 to 30 carbon atoms, a substituted or unsubstituted aromatic hydrocarbon group having 5 to 40 carbon atoms, a substituted or unsubstituted aromatic heterocyclic group having 2 to 40 carbon atoms, a substituted or unsubstituted aralkyl group having 7 to 40 carbon atoms, a substituted or unsubstituted aryloxyl group having 6 to 40 carbon atoms, a substituted or unsubstituted alkoxycarbonyl group having 2 to 30 carbon atoms, a substituted or unsubstituted silyl group having 3 to 40 carbon atoms or carboxyl group. Groups represented by $Ar_1$ and $Ar_2$ and groups represented by $R_1$ and $R_2$ each independently may be bonded to each other and form a cyclic structure.

The foregoing general formulae (1) to (11) may be substituted with substituted or unsubstituted alkyl groups having 1 to 30 carbon atoms or substituted or unsubstituted phenyl group, and in the above general formula (A), A does not represent phenyl group substituted with an arylamino group when the group represented by B is substituted with an arylamino group.

Examples of the substituted or unsubstituted aryl groups having 6 to 30 carbon atoms which is represented by $Ar_1$ to $Ar_3$ include phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxathiazolyl group, diphenylanthranyl group, indolyl group, carbazolyl group, pyridyl group, benzoquinolyl group, fluoranthenyl group and acenaphthofluoranthenyl group.

Examples of the substituted or unsubstituted arylene groups having 6 to 30 carbon atoms which is represented by $Ar_4$ include phenylene group, naphthylene group, anthranylene group, phenanthrylene group, pyrenylene group, coronylene group, biphenylene group, terphenylene group, pyrrolylene group, furanylene group, thiophenylene group, benzothiophenylene group, oxadiazolylene group, diphenyl anthranylene group, indolylene group, carbazolylene group, pyridylene group, benzoquinolylene group, fluoranthenylene group and acenaphthofluoranthenylene group.

Examples of the halogen atom represented by $R_1$ and $R_2$ include fluorine atom, chlorine atom, bromine atom and iodine atom.

Examples of the substituted or unsubstituted amino groups represented by $R_1$ and $R_2$ are groups represented by $-NX^1X^2$. For example, $X^1$ and $X^2$ each independently represent hydrogen atom, methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 4-styrylphenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methyl-biphenylyl group, 4"-t-butyl-p-terphenyl-4-yl group, 2-pyrrolyl group, 3-pyrrolyl group, pyradinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group or 4-t-butyl-3-indolyl group.

Examples of the substituted or unsubstituted alkyl groups having 1 to 30 carbon atoms which are represented by $R_1$ and $R_2$ include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the substituted or unsubstituted alkenyl groups having 2 to 40 carbon atoms which are represented by $R_1$ and $R_2$ include vinyl group, allyl group, 1-butenyl group, 2-butenyl group, 3-butenyl group, 1,3-butadienyl group, 1-methylvinyl group, styryl group, 2,2-diphenylvinyl group, 2,2-ditolylvinyl group, 1,2-ditolylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl-1-butenyl group and 3-phenyl-1-butenyl group.

Examples of the substituted or unsubstituted cycloalkyl groups having 5 to 40 carbon atoms which are represented by $R_1$ and $R_2$ include cyclopropyl group, cyclobutyl group, cyclopentyl group, cyclohexyl group and 4-methylcyclohexyl group.

The substituted or unsubstituted alkoxyl groups having 1 to 30 carbon atoms which are represented by $R_1$ and $R_2$ are represented by —OY. Examples of the group represented by Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the substituted or unsubstituted aromatic hydrocarbon groups having 5 to 40 carbon atoms which are represented by $R_1$ and $R_2$ include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group and 4"-t-butyl-p-terphenyl-4-yl group.

Examples of the substituted or unsubstituted aromatic heterocyclic groups having 2 to 40 carbon atoms which are represented by $R_1$ and $R_2$ include 1-pyrrolyl group, 2-pyrrolyl group, 3-pyrrolyl group, pyradinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzo-furanyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

Examples of the substituted or unsubstituted aralkyl groups having 7 to 40 carbon atoms which are represented by $R_1$ and $R_2$ include benzyl group, 1-phenylethyl group, 2-phenylethyl group, 1-phenyl-isopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group and 1-chloro-2-phenylisopropyl group.

The substituted or unsubstituted aryloxyl groups having 6 to 40 carbon atoms which are represented by $R_1$ and $R_2$ are represented by —OZ. Examples of the group represented by Z include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyradinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzo-furanyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxanyl group, 5-quinoxanyl group, 6-quinoxanyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methyl-pyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group and 4-t-butyl-3-indolyl group.

The substituted or unsubstituted alkoxycarbonyl groups having 2 to 30 carbon atoms which are represented by $R_1$ and $R_2$ are represented by —COOY. Examples of the group represented by Y include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxy-isopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

Examples of the substituted or unsubstituted silyl groups having 3 to 40 carbon atoms which are represented by $R_1$ and $R_2$ include trialkylsilyl groups such as trimethylsilyl group, triethylsilyl group, tripropylsilyl group, tributylsilyl group, tripentylsilyl group, trihexylsilyl group and t-butyldimethylsilyl group, dialkylarylsilyl groups, alkyldiarylsilyl groups and triarylsilyl groups. Examples of the alkyl group and the aryl group include the same groups as those described above.

When the groups represented by $Ar_1$ and $Ar_2$ or the groups represented by $R_1$ and $R_2$ each independently are bonded to each other and form a cyclic structure, examples of the formed structures include the following structures:

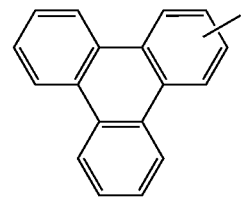

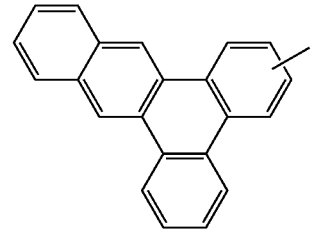

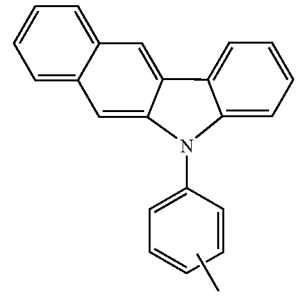

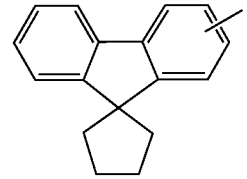

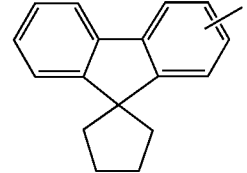
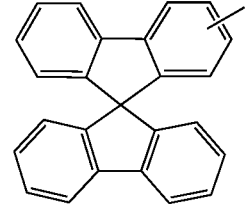

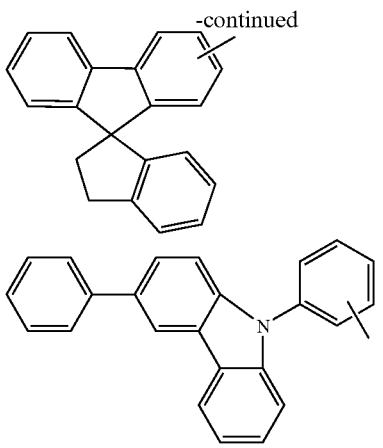

In the foregoing general formula (B), A' represents a group which is selected from groups represented by general formulae (2) to (12):

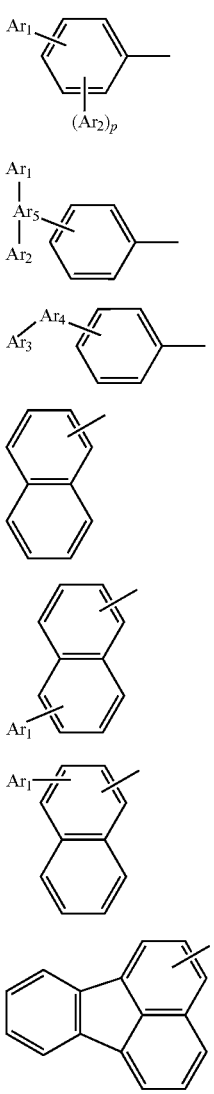

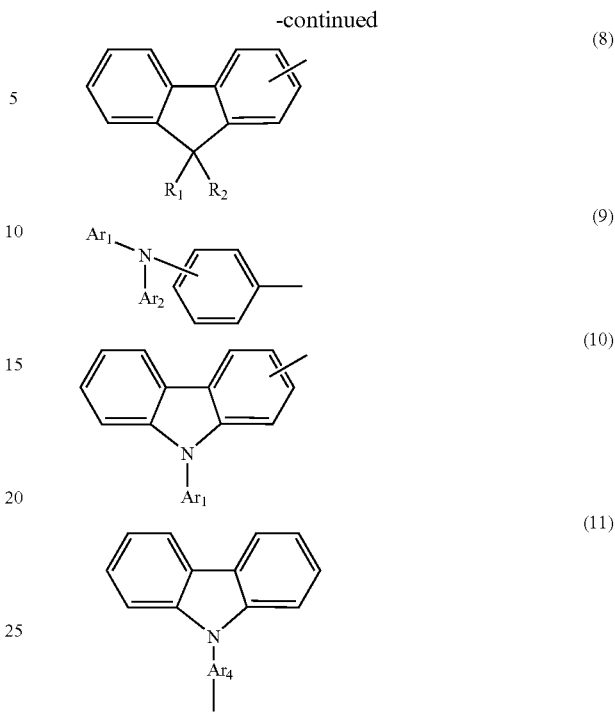

In general formulae (2) to (12), $Ar_1$ to $Ar_3$ each independently represent a substituted or unsubstituted aryl group having 6 to 30 carbon atoms, $Ar_4$ represents a substituted or unsubstituted arylene group having 6 to 30 carbon atoms, $Ar_5$ represents a substituted or unsubstituted trivalent aromatic residue group having 6 to 30 carbon atoms, and $R_1$ and $R_2$ each independently represent hydrogen atom, a halogen atom, hydroxyl group, a substituted or unsubstituted amino group, nitro group, cyano group, a substituted or unsubstituted alkyl group having 1 to 30 carbon atoms, a substituted or unsubstituted alkenyl group having 2 to 40 carbon atoms, a substituted or unsubstituted cycloalkyl group having 5 to 40 carbon atoms, a substituted or unsubstituted alkoxyl group having 1 to 30 carbon atoms, a substituted or unsubstituted aromatic hydrocarbon group having 5 to 40 carbon atoms, a substituted or unsubstituted aromatic heterocyclic group having 2 to 40 carbon atoms, a substituted or unsubstituted aralkyl group having 7 to 40 carbon atoms, a substituted or unsubstituted aryloxyl group having 6 to 40 carbon atoms, a substituted or unsubstituted alkoxycarbonyl group having 2 to 30 carbon atoms, a substituted or unsubstituted silyl group having 3 to 40 carbon atoms or carboxyl group. Groups represented by $Ar_1$ and $Ar_2$ and groups represented by $R_1$ and $R_2$ each independently may be bonded to each other and form a cyclic structure. p in general formula (12) represents 0 or 1.

The foregoing general formulae (2) to (12) may be substituted with substituted or unsubstituted alkyl groups having 1 to 30 carbon atoms or substituted or unsubstituted phenyl group, and in the foregoing general formula (B), A' does not represent phenyl group substituted with an arylamino group when the group represented by B is substituted with an arylamino group.

Examples of the atoms and groups represented by $Ar_1$ to $Ar_5$, $R_1$ and $R_2$ include the atoms and groups described as the examples of the atoms and groups represented by $Ar_1$ to $Ar_5$, $R_1$ and $R_2$ in the foregoing general formulae (1) to (11) in general formula (A).

Examples of the substituent in the groups in general formulae (A) and (B) include halogen atoms, hydroxyl group, substituted or unsubstituted amino groups, nitro group, cyano group, substituted or unsubstituted alkyl groups, substituted or unsubstituted alkenyl groups, substituted or unsubstituted cycloalkyl groups, substituted or unsubstituted alkoxyl groups, substituted or unsubstituted aromatic hydrocarbon groups, substituted or unsubstituted aromatic heterocyclic groups, substituted or unsubstituted aralkyl groups, substituted or unsubstituted aryloxyl groups, substituted or unsubstituted alkoxycarbonyl groups and carboxyl group.

It is preferable that the groups represented by general formulae (1) to (11) in general formula (A) and groups represented by general formulae (2) to (12) in general formula (B) are each independently substituted with an alkyl group having 1 to 30 carbon atoms or a cycloalkyl groups having to 30 carbon atoms.

Examples of the novel aromatic compound represented by general formula (A) or (B) are shown in the following. However, the novel compound is not limited to the compounds shown as the examples.

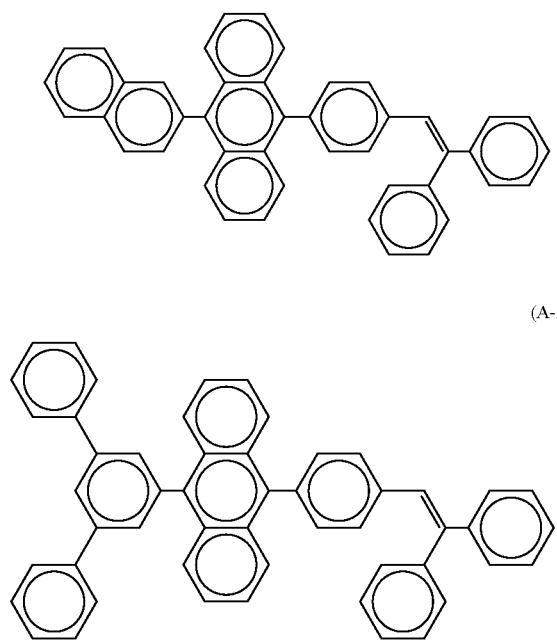

(A-1)

(A-2)

(A-3)

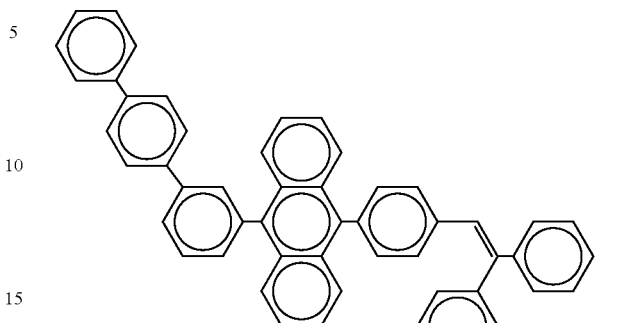

(A-4)

(A-5)

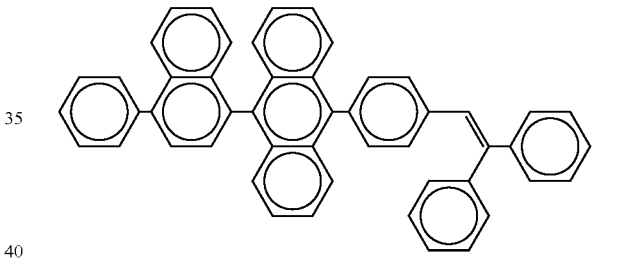

(A-6)

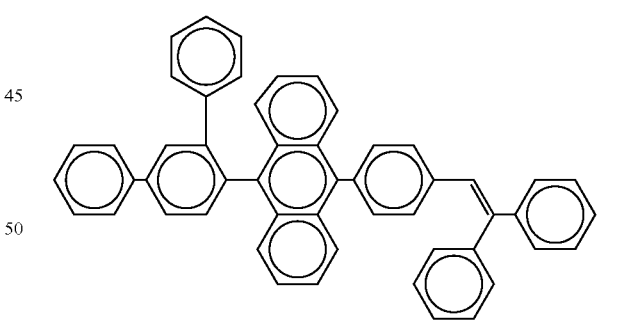

(A-7)

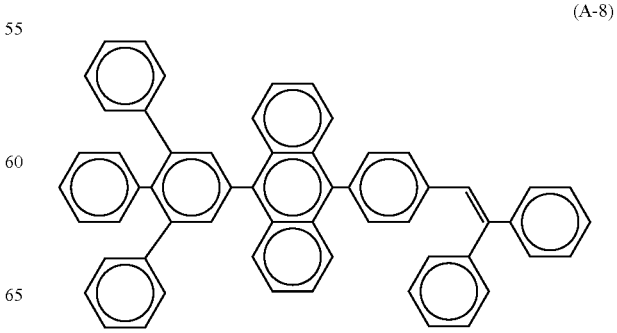

(A-8)

-continued
(A9)
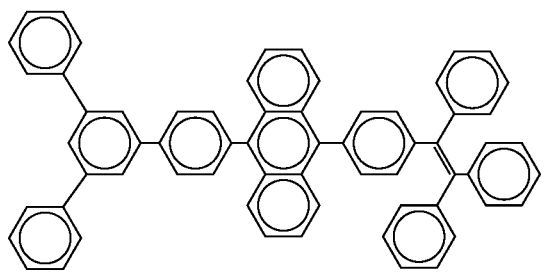
(A-10)
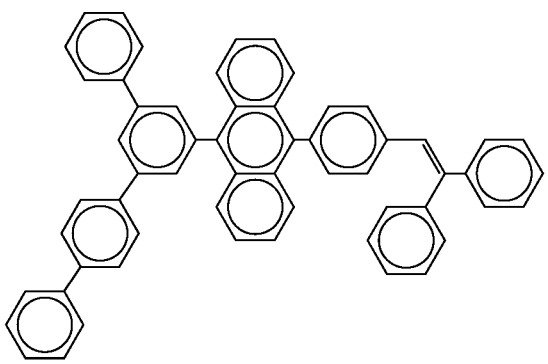
(A-11)
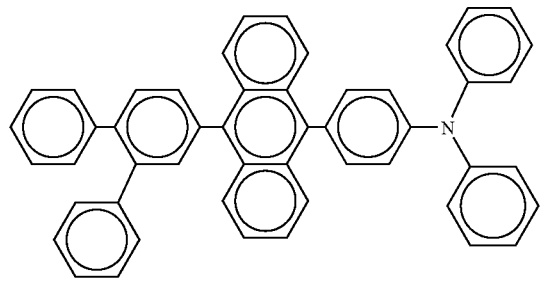
(A-12)
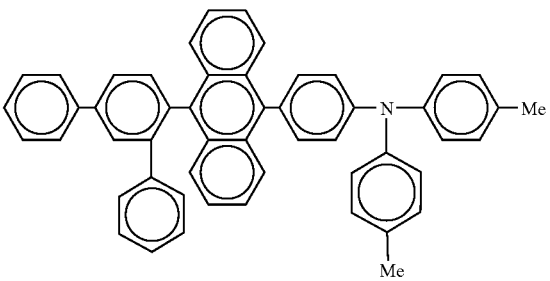
(A-13)
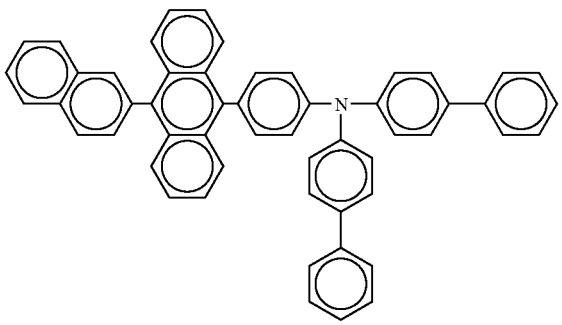
-continued
(A-14)
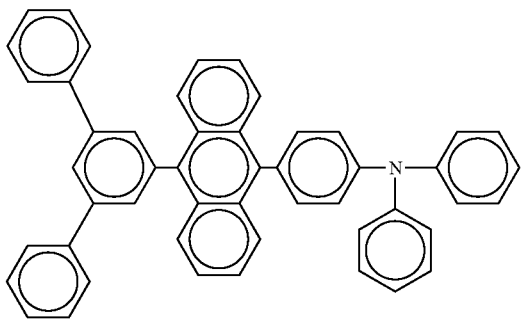
(A15)
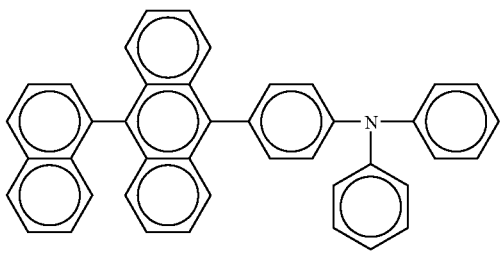
(A16)
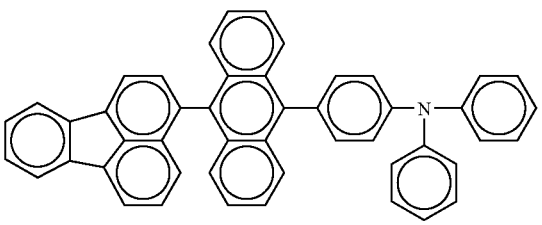
(A17)
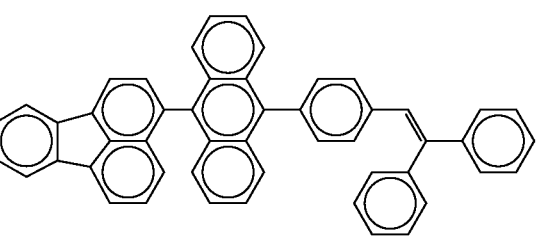
(A18)
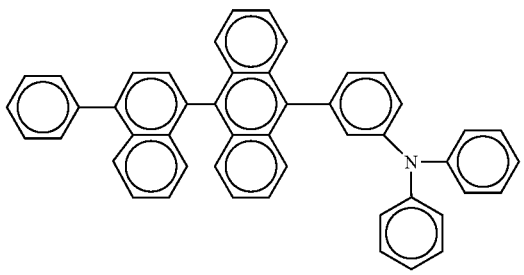

A(19)
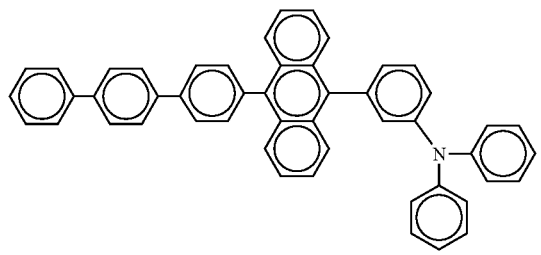
(A20)
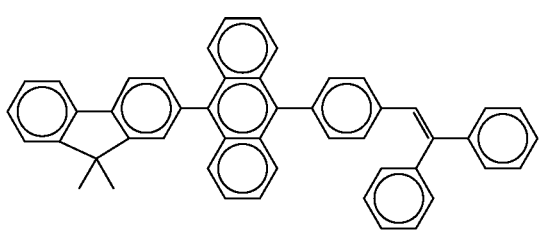
(A21)
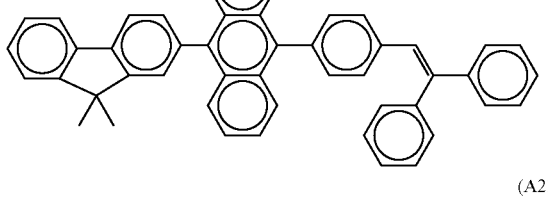
(A22)
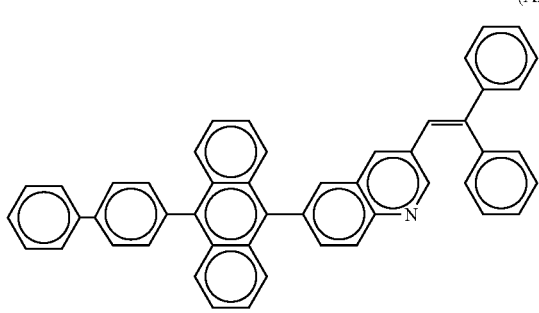
(A23)
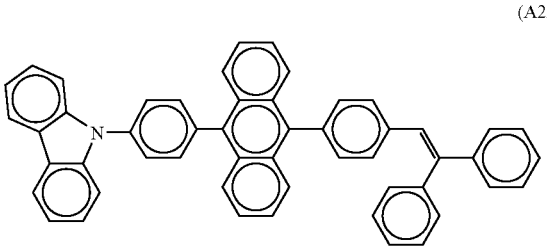
(A24)
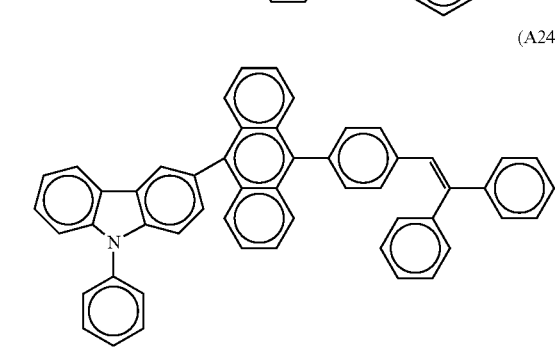
(B1)
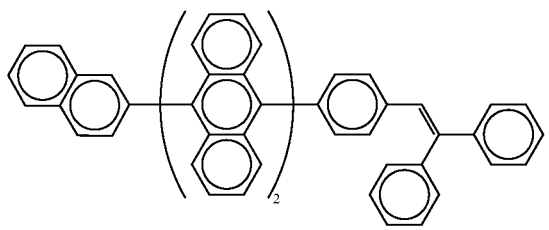
(B2)
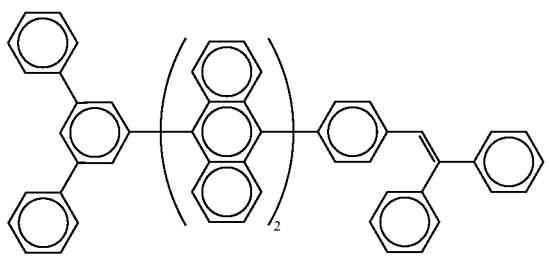
(B3)
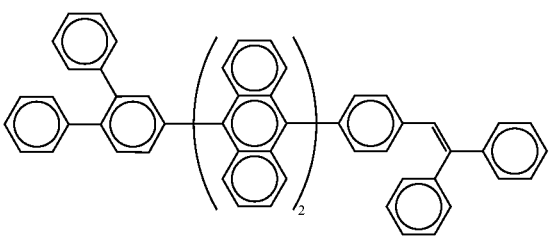
(B4)
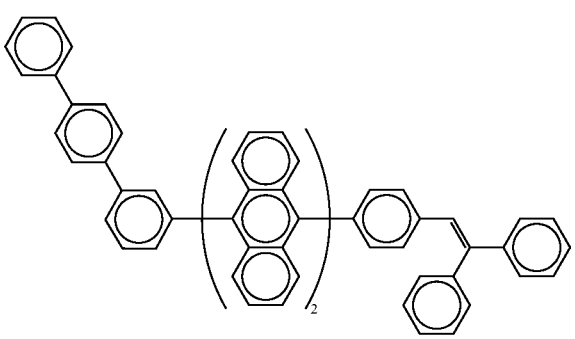
(B5)
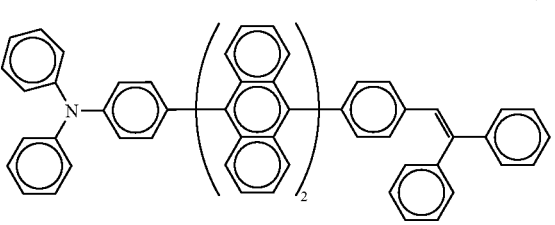
(B6)
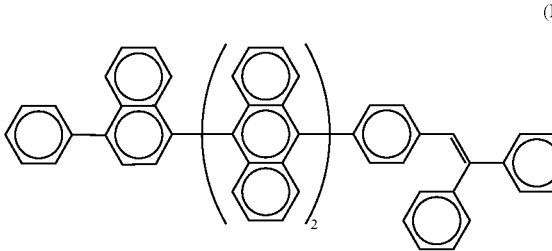

-continued
(B7)
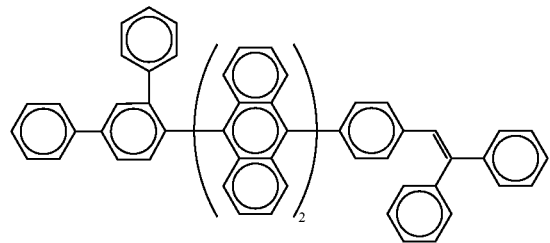
(B8)
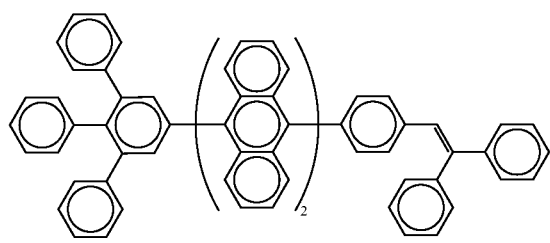
(B9)
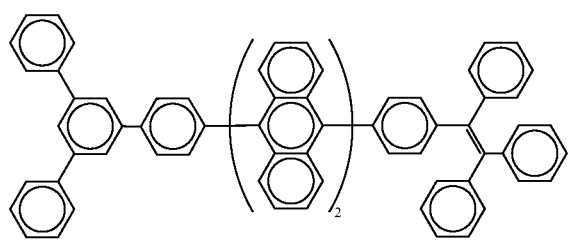
(B10)
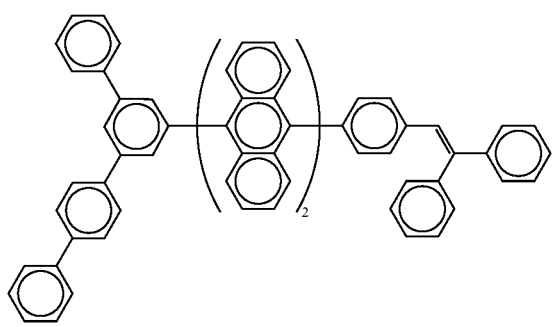
(B11)
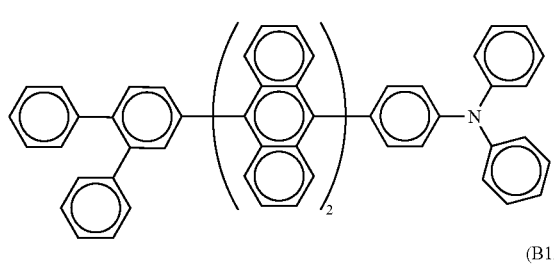
(B12)
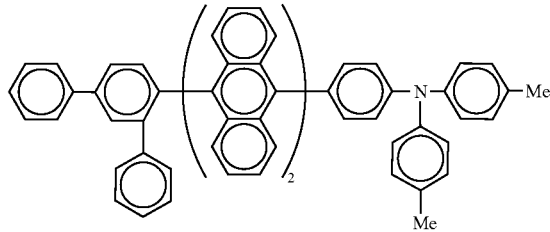
-continued
(B13)
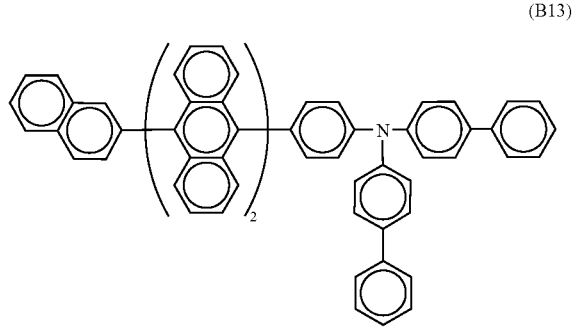
(B14)
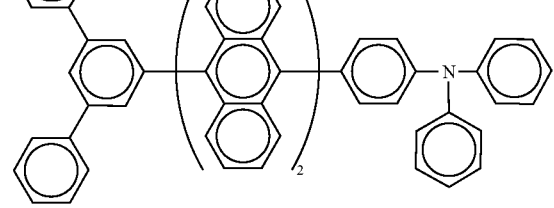
(B15)
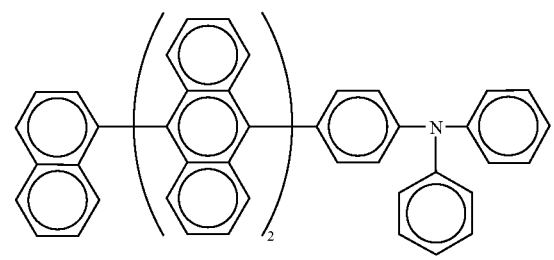
(B-16)
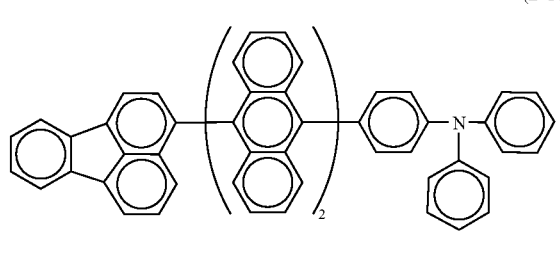
(B-17)
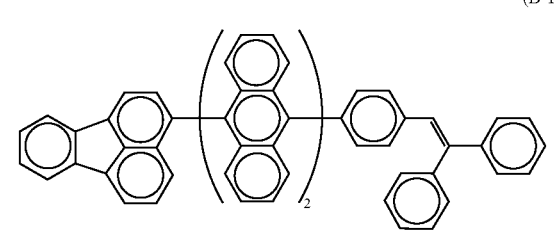

-continued (B-18)
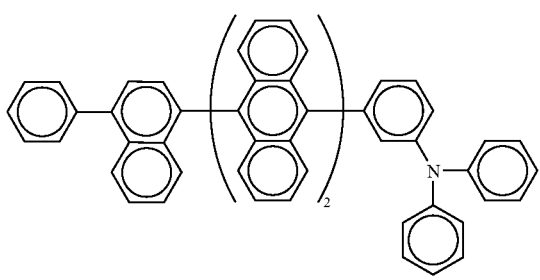

(B-19)
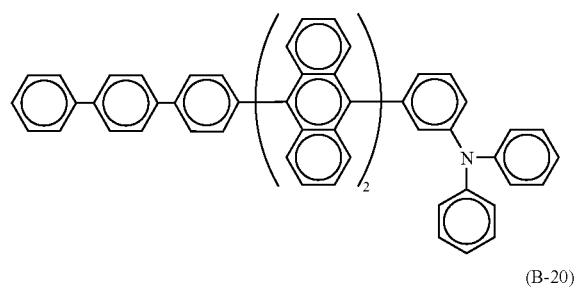

(B-20)
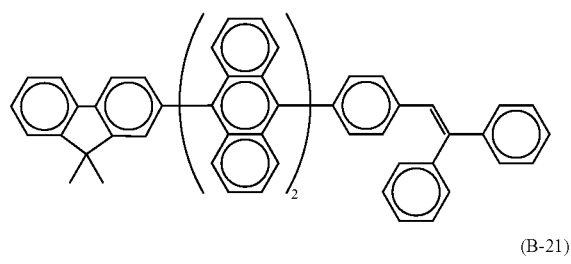

(B-21)
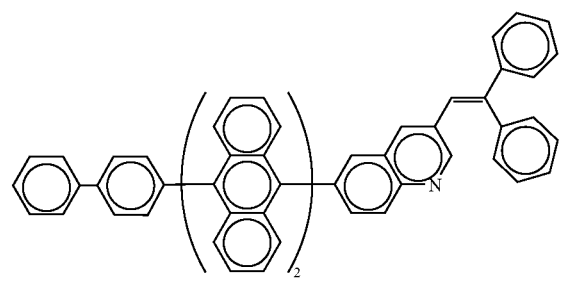

(B-22)
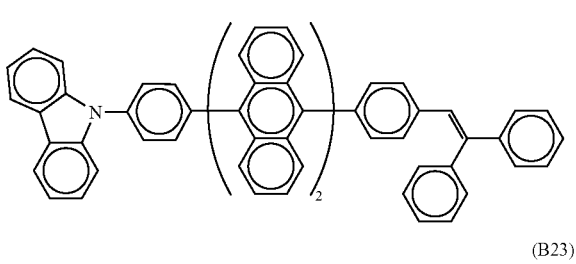

(B-23)
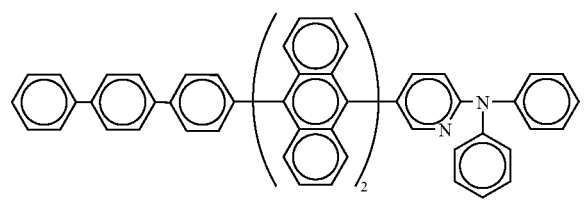

-continued (B-24)
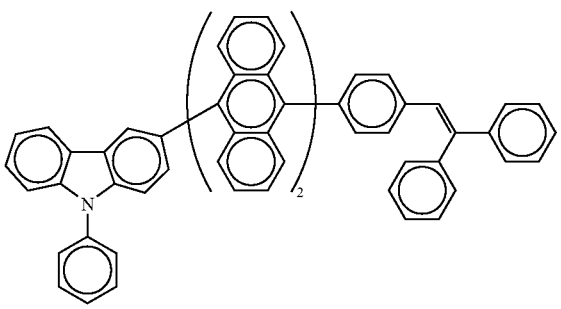

It is preferable that the above aromatic compound represented by general formula (A) or (B) of the present invention is used as a material for organic EL devices.

The organic EL device of the present invention comprises a cathode, an anode and an organic thin film layer comprising at least one layer containing a light emitting layer and sandwiched between the cathode and the anode, wherein at least one layer in the organic thin film layer comprises the aromatic compound represented by general formula (A) or (B) singly or as a component of a mixture.

It is preferable that the organic thin film layer comprises at least one of an electron transporting layer and a hole transporting layer, and at least one of the electron transporting layer and the hole transporting layer comprises the aromatic compound represented by general formula (A) or (B) singly or as a component of a mixture.

It is preferable that the light emitting layer further comprises an arylamine compound and/or a styrylamine compound.

As the arylamine compound, arylamine compounds represented by the following general formula (C) are preferable.

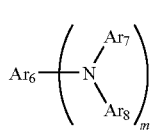

(C)

wherein $Ar_6$ represents an aromatic group having 6 to 40 carbon atoms, $Ar_7$ and $Ar_8$ each independently represent hydrogen atom or an aromatic group having 6 to 20 carbon atoms, and m represents an integer of 1 to 4.

Examples of the aromatic group having 6 to 40 carbon atoms which is represented by $Ar_6$ include aryl groups having 6 to 40 carbon atoms such as phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxadiazolyl group, diphenylanthranyl group, indolyl group, carbazolyl group, pyridyl group, benzoquinolyl group, fluoranthenyl group and acenaphthofluoranthenyl group; and arylene groups having 6 to 40 carbon atoms such as phenylene group, naphthylene group, anthranylene group, phenanthrylene group, pyrenylene group, coronylene group, biphenylene group, terphenylene group, pyrrolylene group, furanylene group, thiophenylene group, benzothiophenylene group, oxadiazolylene group, diphenylanthranylene group, indolylene group, carbazolylene group, pyridylene group, benzoquinolylene group, fluoranthenylene group and acenaphtho-fluoranthenylene group.

The aromatic group having 6 to 40 carbon atoms may be substituted with substituents. Examples of the substituent include alkyl groups having 1 to 6 carbon atoms such as ethyl group, methyl group, i-propyl group, n-propyl group, s-butyl group, t-butyl group, pentyl group, hexyl group, cyclopentyl group and cyclohexyl group; alkoxyl groups having 1 to 6 carbon atoms such as ethoxyl group, methoxyl group, i-propoxyl group, n-propoxyl group, s-butoxyl group, t-butoxyl group, pentoxyl group, hexyloxyl group, cyclopentoxyl group and cyclohexyloxyl group; aryl groups having nuclei having 5 to 40 atoms; amino groups substituted with an aryl group having nuclei having 5 to 40 atoms; ester groups having an aryl group having nuclei having 5 to 40 atoms; ester groups having an alkyl group having 1 to 6 carbon atoms; cyano group; nitro group; and halogen atoms.

Examples of the aromatic group having 6 to 20 carbon atoms which is represented by $Ar_7$ or $Ar_8$ include the compounds having 6 to 20 carbon atoms among the compounds having 6 to 40 carbon atoms which are represented by $Ar_6$.

Examples of the above arylamine compound include triphenylamine, diphenylnaphthylamine and diphenylpyrenylamine.

As the styrylamine compound, styrylamine compounds represented by the following general formula (D) are preferable:

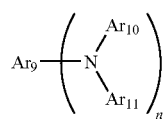

(D)

wherein $Ar_9$ represents a divalent group selected from phenylene group, terphenylene group, stilbene group and distyrylarylene groups, $Ar_{10}$ and $Ar_{11}$ each independently represent hydrogen atom or an aromatic group having 6 to 30 carbon atoms, the groups represented by $Ar_9$, $Ar_{10}$ or $Ar_{11}$ may be substituted, at least one of the groups represented by $Ar_{10}$ and $Ar_{11}$ is substituted with styryl group, and n represents an integer of 1 to 4.

Examples of the substituent to the groups represented by $Ar_9$, $Ar_{10}$ and $Ar_{11}$ include the above substituents to the groups represented by $Ar_6$ in general formula (C).

Examples of the organic EL device of the present invention include organic EL devices having a laminate structure having one or more organic layers laminated between the electrodes. Examples of the structure include structures of an anode/a light emitting layer/a cathode, an anode/a hole transporting layer/a light emitting layer/an electron transporting layer/a cathode, an anode/a hole transporting layer/a light emitting layer/a cathode and an anode/a light emitting layer/an electron transporting layer/a cathode. The aromatic compound of the present invention may be used in any of the layers in the above organic thin film layer and may also be used by doping other hole transporting materials, light emitting materials and electron transporting materials.

In the organic EL device of the present invention, it is preferable that a region transporting electrons or an interface region between the cathode and a layer of an organic thin film comprises a reducing dopant. The reducing dopant is defined as a substance which can reduce the electron transporting compound. Therefore, various types of substances can be used as long as the substance has the specific reducing property. For example, at least one substance selected from the group consisting of alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals and organic complexes of rare earth metals, can be used.

Specific examples of the reducing dopant include at least one alkali metal selected from the group consisting of Na (the work function: 2.36 eV), K (the work function: 2.28 eV), Rb (the work function: 2.16 eV) and Cs (the work function: 1.95 eV) and at least one alkaline earth metal selected from the group consisting of Ca (the work function: 2.9 eV), Sr (the work function: 2.0 to 2.5 eV) and Ba (the work function: 2.52 eV). Among these reducing dopants, reducing dopants having a work function of 2.9 eV or smaller are preferable. It is more preferable that the reducing dopant is at least one alkali metal selected from the group consisting of K, Rb and Cs, still more preferably Rb or Cs, and most preferably Cs. These alkali metals have particularly great reducing ability, and the luminance of emitted light and the life of the organic EL device are improved by adding these alkali metals in a relatively small amount into the region of electron injection. As the reducing dopant having a work function of 2.9 eV or smaller, combinations of two or more alkali metals are also preferable, and combinations including Cs such as combinations of Cs and Na, Cs and K, Cs and Rb, and Cs, Na and K are more preferable. When Cs is include in the combination, the reducing ability can be efficiently exhibited, and the luminance of emitted light and the life of the organic EL device can be improved by adding the combination into the region of electron injection.

The organic EL device of the present invention may further comprises an electron injecting layer constituted with an insulating material or a semiconductor and disposed between the cathode and the organic thin film layer. Due to the electron injecting layer, leak of electric current can be effectively prevented, and the electron injecting property can be improved. It is preferable that at least one metal compound selected from the group consisting of alkali metal chalcogenides, alkaline earth metal chalcogenides, alkali metal halides and alkaline earth metal halides is used as the insulating material. It is preferable that the electron injecting layer is constituted with the alkali metal chalcogenide or the like material since the electron injecting property can be further improved. Examples of the alkali metal chalcogenide include $Li_2O$, LiO, $Na_2S$, $Na_2Se$ and NaO. Preferable examples of the alkaline earth metal chalcogenide include CaO, BaO, SrO, BeO, BaS and CaSe. Examples of the alkali metal halide include LiF, NaF, KF, LiCl, KCl and NaCl. Examples of the alkaline earth metal halide include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or as a combination of two or more. It is preferable that the inorganic compound constituting the electron transporting layer is in the form of a fine crystalline or amorphous insulating thin film. When the electron transporting layer is constituted with the above insulating thin film, a more uniform thin film can be formed and defective pixels such as dark spots can be decreased. Examples of the inorganic compound include the alkali metal chalcogenides, the alkaline earth metal chalcogenides, the alkali metal halides and the alkaline earth metal halides which are described above.

The anode of the organic EL device plays the role of injecting holes into the hole transporting layer or the light emitting layer. It is effective that the anode has a work function of 4.5 eV or greater. Examples of the material of the anode used in the present invention include indium tin oxide alloys (ITO), tin oxides (NESA), gold, silver, platinum and copper. As the cathode, a material having a small work function is preferable so that electrons can be injected into the electron transporting layer or the light emitting layer.

The process for forming the layers in the organic EL device of the present invention is not particularly limited. A conventional process such as the vacuum vapor deposition process and the spin coating process can be used. The organic thin film layer comprising the compound represented by the above general formula (A) or (B) can be formed in accordance with the vacuum vapor deposition process, the molecular beam epitaxy process (the MBE process) or, using a solution prepared by dissolving the compound into a solvent, in accordance with a conventional coating process such as the dipping process, the spin coating process, the casting process, the bar coating process and the roll coating process.

The thickness of each layer in the organic thin film layer in the organic EL device of the present invention is not particularly limited. In general, an excessively thin layer tends to have defects such as pin holes, and an excessively thick layer requires a high applied voltage to decrease the efficiency. Therefore, a thickness in the range of several nm to 1 µm is preferable.

As described above, by using the novel aromatic compound of the present invention for the organic thin film layer of the organic EL device of the present invention, the organic EL device which exhibits a great luminance of emitted light, a great efficiency of light emission and a high purity of color, emits bluish light, is excellent in stability at high temperatures and has a long life can be obtained. This organic EL device can be advantageously used for a photosensitive member for electronic photograph, a planar light emitting member such as a flat panel display of wall televisions, a back light of copiers, printers and liquid crystal displays, a light source for instruments, a display panel, a marking light and an accessory.

The present invention will be described more specifically with reference to examples in the following. However, the present invention is not limited to the examples.

SYNTHESIS EXAMPLE 1

Synthesis of Compound (A1)

(1) Synthesis of 9-(2-naphthyl)anthracene

Under an atmosphere of argon, 9-bromoanthracene (3 g, 12 mmole), 2-naphthaleneboric acid (2.4 g, 14 mmole, 1.2 eq) and tetrakis-(triphenylphosphine)palladium(0) (0.28 g, 0.24 mmole, 2% Pd) were suspended in dimethoxyethane (40 ml). To the obtained suspension, a 2M aqueous solution of sodium carbonate (4.5 g, 42 mmole, 3 eq/20 ml) was added, and the resultant mixture was refluxed for 10 hours. The obtained reaction mixture was filtered and washed with water and methanol, and a light yellow solid substance was obtained. The solid substance was suspended in boiling dimethoxyethane (30 ml), cooled while being left standing, filtered and washed with dimethoxyethane and acetone, and a gray solid substance (82% crude) was obtained. This solid substance was purified using a short column (silica gel/dichloroethane), and a light yellow solid substance (2.7 g, the yield: 74%) was obtained. The obtained product was identified to be 9-(2-naphthyl)anthracene in accordance with $^1$H-NMR.

$^1$H-NMR (CDCl$_3$, TMS) δ: 7.2-7.7 (9H, m), 7.8-8.1 (6H, m), 8.51 (1H, s).

(2) Synthesis of 9-bromo-10-(2-naphthyl)anthracene 9-(2-Naphthyl)anthracene (2.7 g, 8.9 mmole) was suspended in anhydrous N,N-dimethylformamide (DMF) (50 ml). To the obtained suspension, an anhydrous DMF solution (6 ml) of N-bromosuccinimide (NBS) (1.7 g, 9.6 ml, 1.1 eq) was added, and the resultant mixture was stirred at the room temperature for 10 hours and then left standing for one night. The reaction mixture was diluted with water (50 ml). The formed solid substance was separated by filtration and washed with methanol, and a light yellow solid substance (3.2 g, the yield: 94%) was obtained. The obtained product was identified to be 9-bromo-10-(2-naphthyl)anthracene in accordance with $^1$H-NMR.

$^1$H-NMR (CDCl$_3$, TMS) δ: 7.2-7.7 (9H, m), 7.8-8.1 (4H, m), 8.62 (2H, d, J=8 Hz).

(3) Synthesis of 9-(4-(2,2-diphenylvinyl)phenyl)-10-(2-naphthyl)anthracene (Compound (A1)

Under an atmosphere of argon, 9-bromo-10-(2-naphthyl)anthracene (3.2 g, 8.4 mmole), 4-(2,2diphenylvinyl)phenylboric acid (2.8 g, 9.3 mmole, 1.1 eq) and tetrakis(triphenylphosphine)palladium(0) (0.19 g, 0.16 mmole, 2% Pd) were suspended in toluene (30 ml). To the obtained suspension, a 2M aqueous solution of sodium carbonate (3 g, 28 mmole, 3 eq/15 ml) was added, and the resultant mixture was refluxed for 10 hours. The obtained reaction mixture was filtered and washed with toluene, water and methanol, and a light yellow solid substance (3.7 g) was obtained. The solid substance was suspended in boiling toluene (40 ml), cooled while being left standing and filtered, and a light yellow solid substance (3.4 g, the yield: 73%) was obtained. The result of examination of the obtained product in accordance with $^1$H-NMR was as follows:

$^1$H-NMR (CDCl$_3$, TMS) δ: 7.15 (1H, s), 7.2-7.4 (17H, m), 7.5-7.8 (8H, m), 7.8-8.1 (4H, m).

The obtained solid substance (3.4 g) was purified by sublimation at 340° C./10$^{-6}$ Torr for 1 hour, and a light yellow substance (2.9 g) was obtained. It was confirmed in accordance with the field desorption mass analysis (FDMS) that the obtained product was the object compound (Compound (A1)). The results of measurements of the energy gap Eg, the ionization potential Ip and the glass transition temperature Tg are also shown in the following.

FDMS: calcd. for $C_{44}H_{30}$=558, found m/z=558 (M+, 100)
λmax: 397, 378, 359 nm (PhMe)
Fmax: 438 nm (PhMe: λex=397 nm)
Ip=5.71 eV (100 nW, 27 Y/eV)
Tg=108° C.

SYNTHESIS EXAMPLE 2

Synthesis of Compound (A2)

(1) Synthesis of 9-(3,5-dibromophenyl)anthracene

Under an atmosphere of argon, 9-iodoanthracene (8.7 g, 29 mmole, 1.1 eq), 3,5-dibromophenylboric acid (7.3 g, 26 mmole) and tetrakis-(triphenylphosphine)palladium(0) (0.67 g, 0.58 mmole, 2% Pd) were suspended in toluene (80 ml). To the obtained suspension, a 2M aqueous solution of sodium carbonate (8.3 g, 78 mmole, 3 eq/40 ml) was added, and the resultant mixture was refluxed for 10 hours. An organic layer was separated from the obtained reaction mixture, washed with a saturated aqueous solution of sodium chloride and dried with magnesium sulfate. After the solvent was removed by distillation, a yellow solid substance was obtained and, then, the obtained solid substance was suspended in dichloromethane (20 ml). The solid component was separated by filtration and washed with a mixed solution of dichloromethane and hexane, and a light yellow solid substance (5.1 g, the yield: 48%, the first crop) was obtained. The filtrate was purified in accordance with the column chromatography (silica gel/hexane, hexane+5% dichloromethane), and a light yellow solid substance (4.2 g, the yield: 39%, the second crop) was obtained. The yellow solid substances of the first crop and the second crop were combined (9.3 g, the yield: 87%). The obtained product was identified to be 9-(3,5-dibromophenyl)anthracene in accordance with $^1$H-NMR.

$^1$H-NMR (CDCl$_3$, TMS) δ: 7.3-7.6 (8H, m), 7.85 (1H, t, J=2 Hz), 8.0-8.1 (2H, m), 8.49 (1H, s).

(2) Synthesis of 9-(3,5-diphenylphenyl)anthracene

Under an atmosphere of argon, 9-(3,5-dibromophenyl)anthracene (5 g, 12 mmole), phenylboric acid (4.4 g, 36 mmole, 3 eq) and tetrakis(triphenylphosphine)palladium(0) (0.55 g, 0.48 mmole, 2% Pd) were dissolved in toluene (100 ml). To the obtained solution, a 2M aqueous solution of sodium carbonate (11 g, 0.10 moles, 3 eq/50 ml) was added, and the resultant mixture was refluxed for 10 hours. The obtained reaction mixture was filtered, and an organic layer was separated from the filtrate, washed with a saturated aqueous solution of sodium chloride (50 ml) and dried with magnesium sulfate. After the solvent was removed by distillation, a black oily substance was obtained. The obtained oily substance was purified in accordance with the column chromatography (silica gel/hexane, hexane+3% dichloromethane, hexane +10% dichloromethane in the final step), and a light yellow amorphous solid substance (3.6 g, 74%) was obtained. The obtained product was identified to be 9-(3,5-diphenylphenyl)anthracene in accordance with $^1$H-NMR and FDMS.

$^1$H-NMR (CDCl$_3$, TMS) δ: 7.3-7.6 (10H, m), (1H, s), 7.7-7.9 (8H, m), 8.01 (1H, s), 8.05 (2H, dd, J=9 Hz, 2 Hz), 8.52 (1H, s).

FDMS: calcd. for C$_{32}$H$_{22}$=406, found m/z=406 (M+, 100)

(3) Synthesis of 9-bromo-10-(3,5-diphenylphenyl)anthracene 9-(3,5-Diphenylphenyl)anthracene (3.6 g, 8.9 mmole) was suspended in anhydrous DMF (60 ml). After an anhydrous DMF solution (7 ml) of NBS (1.9 g, 11 mmole, 1.2 eq) was added, the resultant mixture was stirred at the room temperature for 10 hours and then left standing for one night. The reaction mixture was diluted with water (50 ml). The formed solid substance was separated by filtration and washed with methanol, and a light yellow solid substance (3.9 g, the yield: 90%) was obtained. The obtained product was identified to be 9-bromo-10-(3,5-diphenylphenyl)anthracene in accordance with $^1$H-NMR.

$^1$H-NMR (CDCl$_3$, TMS) δ: 7.3-7.9 (18H, m), 8.01 (1H, t, J=2 Hz), 8.62 (2H, d, J=9 Hz).

(4) Synthesis of 9-(4-(2,2-diphenylvinyl)phenyl)-10-(3,5-diphenylphenyl)-anthracene (Synthesis of Compound (A2))

Under an atmosphere of argon, 9-bromo-10-(3,5-diphenylphenyl)anthracene (3.9 g, 8.0 mmole), 4-(2,2-diphenylvinyl)phenylboric acid (2.7 g, 9.0 mmole, 1.1 eq) and tetrakis(triphenylphosphine)palladium(0) (0.18 g, 0.16 mmole, 2% Pd) were suspended in toluene (30 ml). To the obtained suspension, a 2M aqueous solution of sodium carbonate (2.9 g, 27 mmole, 3 eq/15 ml) was added, and the resultant mixture was refluxed for 10 hours. An organic layer was separated from the reaction mixture, washed with a saturated aqueous solution of sodium chloride (30 ml) and dried with magnesium sulfate. After the solvent was removed by distillation, a brown solid substance was obtained. The obtained solid substance was purified in accordance with the column chromatography (silica gel/hexane+10% dichloromethane, hexane+ 20% dichloromethane), and a white solid substance (4.3 g, the yield: 81%) was obtained. The result of examination of the obtained product in accordance with $^1$H-NMR was as follows:

$^1$H-NMR (CDCl$_3$, TMS) δ: 7.15 (1H, s), 7.2-7.5 (24H, m), 7.7-7.9 (10H, m), 8.02 (1H, t, J=2 Hz).

The obtained solid substance (4.3 g) was purified by sublimation at 360° C./10$^{-6}$ Torr for 1 hour, and a light yellow substance (3.2 g) was obtained. It was confirmed in accordance with FDMS that the obtained product was the object compound (Compound (A2)). The results of measurements of Eg, Ip and Tg are also shown in the following.

FDMS: calcd. for C$_{52}$H$_{30}$=660, found m/z=660 (M+, 100)
λmax: 397, 377, 359 nm (PhMe)
Fmax: 435 nm (PhMe: λex=397 nm)
Ip=5.82 eV (100 nW, 27 Y/eV)
Tg=120° C.

SYNTHESIS EXAMPLE 3

Synthesis of Compound (A3)

(1) Synthesis of 9-(3,4-dichlorophenyl)anthracene

Under an atmosphere of argon, 3,4-dichlorophenylboric acid (2.7 g, 14 mmole, 1.1 eq), 9-bromoanthracene (3.3 g, 13 mmole) and tetrakis(triphenylphosphine)palladium(0) (0.3 g, 0.26 mmole, 2% Pd) were suspended in toluene (40 ml). To the obtained suspension, a 2M aqueous solution of sodium carbonate (4.5 g, 42 mmole, 3 eq/20 ml) was added, and the resultant mixture was refluxed for 10 hours. The reaction mixture was filtered to remove Pd black, and an organic layer was separated from the filtrate, washed with a saturated aqueous solution of sodium chloride (30 ml) and dried with magnesium sulfate. After the solvent was removed by distillation, a light brown oily substance was obtained. When a small amount of methanol was added to the obtained oily substance and the wall of the flask was rubbed, crystals were formed. The formed crystals were separated by filtration and washed with methanol, and a light yellow solid substance (3.7 g, the yield: 88%) was obtained. The obtained product was identified to be 9-(3,4-dichlorophenyl)anthracene in accordance with $^1$H-NMR.

$^1$H-NMR (CDCl$_3$, TMS) δ: 7.2-7.7 (9H, m), 8.02 (2H, dd, J=7 Hz, 2 Hz), 8.48 (1H, s).

(2) Synthesis of 9-(3,4-diphenylphenyl)anthracene

Under an atmosphere of argon, phenylboric acid (3.6 g, 30 mmole, 2.7 eq), 9-(3,4-dichlorophenyl)anthracene (3.7 g, 11 mmole) and dichlorobis(triphenylphosphine)nickel(II) (0.72 g, 1.1 mmole, 5% Ni), triphenylphosphine (0.58 g, 2.2 mmole, 2 eq to Ni) and potassium phosphate hydrate (16 g, 60 mmole, 2 eq) were suspended in anhydrous toluene (80 ml), and the obtained suspension was heated at 80° C. for 10 hours.

To the reaction mixture, water (50 ml) was added, and insoluble components were removed by filtration. An organic layer was separated from the filtrate, washed with a saturated aqueous solution of sodium chloride (30 ml) and dried with magnesium sulfate. After the solvent was removed by distillation, a light brown oily substance was obtained. The obtained oily substance was purified in accordance with the column chromatography (silica gel/hexane+10% dichloromethane, hexane+20% dichloromethane, hexane+30% dichloromethane in the final step), and a white solid substance (3.7 g, the yield: 83%) was obtained. The obtained product was identified to be 9-(3,4-diphenylphenyl)anthracene in accordance with $^1$H-NMR and FDMS.

$^1$H-NMR (CDCl$_3$, TMS) δ: 7.1-7.7 (17H, m), 7.8-8.1 (4H, m), 8.49 (1H, s).

FDMS: calcd. for C$_{32}$H$_{22}$=406, found m/z=406 (M+, 100).

(3) Synthesis of (3,4-diphenylphenyl)-10-bromoanthracene 9-(3,4-Diphenylphenyl)anthracene (3.7 g, 9.1 mmole) was suspended in anhydrous DMF (50 ml). After an anhydrous DMF solution (10 ml) of NBS (1.8 g, 10 mmole, 1.1 eq) was added, the resultant mixture was heated at 55° C. for 5 minutes so that the reaction mixture became a homogeneous solution. The obtained solution was stirred at the room temperature for 4 hours and then left standing for one night. The reaction mixture was diluted with water (50 ml). The formed solid substance was separated by filtration and washed with methanol, and a light yellow solid substance (4.2 g, the yield: 95%) was obtained. The obtained product was identified to be 9-(3,4-diphenylphenyl)-10-bromoanthracene in accordance with $^1$H-NMR.

$^1$H-NMR (CDCl$_3$, TMS) δ: 0.2-7.7 (17H, m), 7.85 (2H, d, J=8 Hz), 8.61 (2H, d, J=8 Hz).

(4) Synthesis of 9-(3,4-diphenylphenyl)-10-(4-(2,2-diphenylvinyl)phenyl)anthracene (Synthesis of Compound (A3))

Under an atmosphere of argon, 9-(3,4-diphenylphenyl)-10-bromoanthracene (3.0 g, 6.2 mmole), 4-(2,2-diphenylvinyl)phenylboric acid (2.0 g, 6.7 mmole, 1.1 eq) and tetrakis(triphenylphosphine)palladium(0) (0.14 g, 0.12 mmole, 2% Pd) were suspended in toluene (20 ml). To the obtained suspension, a 2M aqueous solution of sodium carbonate (2.1 g, 20 mmole, 3 eq/10 ml) was added, and the resultant mixture was refluxed for 10 hours. The reaction mixture was filtered and washed with water and methanol, and a light yellow solid substance (3.7 g) was obtained. The obtained solid substance was suspended in boiling toluene (40 ml). After the suspension was cooled while being left standing, the suspension was filtered, and a light yellow solid substance (3.6 g, the yield: 88%) was obtained. The result of examination of the obtained product in accordance with $^1$H-NMR was as follows:

$^1$H-NMR (CDCl$_3$, TMS) δ: 0-7.9 (36H, m), all-H.

The obtained solid substance (3.6 g) was purified by sublimation at 340° C./10$^{-6}$ Torr for 1 hour, and a light yellow solid substance (2.1 g) was obtained. It was confirmed in accordance with FDMS that the obtained product was the object compound (Compound (A3)). The results of measurements of Eg, Ip and Tg are also shown in the following.

FDMS: calcd. for C$_{52}$H$_{36}$=660, found m/z=660 (M+, 100)
λmax: 398, 378, 359 nm (PhMe)
Fmax: 437 nm (PhMe: λex=398 nm)
Ip=5.82 eV (100 nW, 64 Y/eV)
Tg=122° C.

SYNTHESIS EXAMPLE 4

Synthesis of Compound (A4)

(1) Synthesis of 9-(3-chlorophenyl)anthracene

Under an atmosphere of argon, 3-chlorophenylboric acid (3.3 g, 21 mmole, 1.1 eq), 9-bromoanthracene (5.0 g, 19 mmole) and tetrakis-(triphenylphosphine)palladium(0) (0.5 g, 0.43 mmole, 2% Pd) were suspended in toluene (60 ml). To the obtained suspension, a 2M aqueous solution of sodium carbonate (6.8 g, 64 mmole, 3 eq/35 ml) was added, and the resultant mixture was refluxed for 10 hours. An organic layer was separated from the filtrate, washed with a saturated aqueous solution of sodium chloride (30 ml) and dried with magnesium sulfate. After the solvent was removed by distillation, a yellow oily substance was obtained. The obtained oily substance was purified in accordance with the column chromatography (silica gel/hexane+5% dichloromethane), and a light yellow solid substance (5.2 g, the yield: 95%) was obtained. The obtained product was identified to be 9-(3-chlorophenyl)anthracene in accordance with $^1$H-NMR.

$^1$H-NMR (CDCl$_3$, TMS) δ: 0.2-7.7 (10H, m), 7.7-7.8 (2H, m), 8.48 (1H, s).

(2) Synthesis of 9-(3-(4-phenylphenyl)phenyl)anthracene

Under an atmosphere of argon, 4-biphenylboric acid (3.6 g, 18 mmole, 1.3 eq), 9-(3-chlorophenyl)anthracene (4.1 g, 14 mmole), dichloro(1,1'-bis(diphenylphosphino)ferrocene)nickel(II) (0.3 g, 0.44 mmole, 3% Ni) and anhydrous potassium phosphate (10 g, 47 mmole, 2.7 eq) were suspended in anhydrous dioxane (70 ml), and the obtained suspension was heated at 90° C. for 7 hours. To the reaction mixture, water (50 ml) and toluene (100 ml) were added. An organic layer was separated, washed with a saturated aqueous solution of sodium chloride (30 ml) and dried with magnesium sulfate. After the solvent was removed by distillation, a light brown solid substance was obtained. The obtained solid substance was suspended in a boiling mixture of ethanol (50 ml) and toluene (10 ml). After the resultant mixture was cooled while being left standing, the mixture was filtered and washed with ethanol, and a white solid substance (4.8 g, the yield: 84%) was obtained. The obtained product was identified to be 9-(3-(4-phenylphenyl)phenyl)anthracene in accordance with $^1$H-NMR.

$^1$H-NMR (CDCl$_3$, TMS) δ: 0.3-7.8 (19H, m), 8.03 (2H, d, J=7 Hz), 8.49 (1H, s).

(3) Synthesis of 9-(3-(4-phenylphenyl)phenyl)-10-bromoanthracene 9-(3-(4-Phenylphenyl)phenyl)anthracene (4.8 g, 12 mmole) was suspended in anhydrous DMF (70 ml). After an anhydrous DMF solution (15 ml) of NBS (2.3 g, 13 mmole, 1.1 eq) was added, the resultant mixture was heated at 40° C. for 15 minutes so that the reaction mixture became a homogeneous solution. The obtained solution was stirred at the room temperature for 7 hours and then left standing for one night. The reaction mixture was diluted with water (50 ml). The formed solid substance was separated by filtration and washed with methanol, and a light yellow solid substance (5.2 g, the yield: 89%) was obtained. The obtained product was identified to be 9-(3-(4-phenylphenyl)phenyl)-10-bromoanthracene in accordance with $^1$H-NMR.

$^1$H-NMR (CDCl$_3$, TMS) δ: 7.3-7.8 (19H, m), 8.61 (2H, d, J=9 Hz).

4) Synthesis of 9-(3-(4-phenylphenyl)phenyl)-10-(4-(2,2-diphenylvinyl)phenyl)anthracene (Synthesis of Compound (A4))

Under an atmosphere of argon, 9-(3-(4-phenylphenyl)phenyl)-10-bromoanthracene (3.0 g, 6.2 mmole), 4-(2,2-diphenylvinyl)phenylboric acid (2.0 g, 6.7 mmole, 1.1 eq) and tetrakis(triphenylphosphine)palladium(0) (0.14 g, 0.12 mmole, 2% Pd) were suspended in toluene (20 ml). To the obtained suspension, a 2M aqueous solution of sodium carbonate (2.1 g, 20 mmole, 3 eq/10 ml) was added, and the resultant mixture was refluxed for 10 hours. The reaction mixture was filtered and washed with water and methanol, and a light yellow solid substance was obtained. The obtained solid substance was suspended in boiling toluene (30 ml). After the suspension was cooled while being left standing, the suspension was filtered, and a light yellow solid substance (3.0 g, the yield: 73%) was obtained. The result of examination of the obtained product in accordance with $^1$H-NMR was as follows:

$^1$H-NMR (CDCl$_3$, TMS) δ: 7.15 (1H, s), 7.2-7.4 (22H, m), 7.6-7.8 (13H, m).

The obtained solid substance (3.0 g) was purified by sublimation at 340° C./10$^{-6}$ Torr for 1 hour, and a light yellow solid substance (2.6 g) was obtained. It was confirmed in accordance with FDMS that the obtained product was the object compound (Compound (A4)). The results of measurements of Eg, Ip and Tg are also shown in the following.

FDMS: calcd. for C$_{52}$H$_{36}$=660, found m/z=660 (M+, 100)
λmax: 397, 377, 358 nm (PhMe)
Fmax: 434 nm (PhMe: λex=397 nm)
Ip=5.83 eV (100 nW, 82 Y/eV)
Tg=115° C.

SYNTHESIS EXAMPLE 5

(Synthesis of Compound (A5))

(1) Synthesis of 9-(4-chlorophenyl)anthracene

Under an atmosphere of argon, 4-chlorophenylboric acid (5.0 g, 32 mmole, 1.1 eq), 9-bromoanthracene (7.5 g, 29 mmole) and tetrakis(triphenylphosphine)palladium(0) (0.7 g, 0.61 mmole, 2% Pd) were suspended in toluene (100 ml). To the obtained suspension, a 2M aqueous solution of sodium carbonate (10 g, 94 mmole, 3 eq/50 ml) was added, and the resultant mixture was refluxed for 10 hours. The reaction mixture was filtered to remove Pd black, and an organic layer was separated from the filtrate, washed with a saturated aqueous solution of sodium chloride (30 ml) and dried with magnesium sulfate. After the solvent was removed by distillation, a white solid substance was obtained. The obtained solid substance was suspended in boiling ethanol (50 ml). After the mixture was cooled while being left standing, the mixture was filtered and washed with ethanol, and a white solid substance (7.7 g, the yield: 92%) was obtained. The obtained product was identified to be 9-(4-chlorophenyl)anthracene in accordance with $^1$H-NMR.

$^1$H-NMR (CDCl$_3$, TMS) δ: 7.2-7.7 (10H, m), 8.02 (2H, dd, J=7 Hz, 2 Hz), 8.48 (1H, s).

(2) Synthesis of 9-(4-chlorophenyl)-10-bromoanthracene 9-(4-Chlorophenyl)anthracene (4.0 g, 14 mmole) was suspended in anhydrous DMF (60 ml). After an anhydrous DMF solution (10 ml) of NBS (2.5 g, 14 mmole, 1 eq) was added, the resultant mixture was stirred at the room temperature for 7 hours and then left standing for one night. The reaction mixture was diluted with water (70 ml). The formed solid substance was separated by filtration and washed with methanol, and a light yellow solid substance (4.6 g, the yield: 89%) was obtained. The obtained product was identified to be 9-(4-chlorophenyl)-10-bromoanthracene in accordance with $^1$H-NMR.

$^1$H-NMR (CDCl$_3$, TMS) δ: 7.3-7.7 (10H, m), 8.60 (2H, d, J=9 Hz).

(3) Synthesis of 9-(4-chlorophenyl)-10-(4-(2,2-diphenylvinyl)phenyl)anthracene

Under an atmosphere of argon, 9-(4-chlorophenyl)-10-bromoanthracene (2.0 g, 5.4 mmole), 4-(2,2-diphenylvinyl)phenylboric acid (1.8 g, 6.0 mmole, 1.1 eq) and tetrakis(triphenylphosphine)palladium(0) (0.12 g, 0.10 mmole, 2% Pd) were suspended in toluene (20 ml). To the obtained suspension, a 2M aqueous solution of sodium carbonate (1.9 g, 18 mmole, 3 eq/10 ml) was added, and the resultant mixture was refluxed for 10 hours. The reaction mixture was filtered and washed with water and methanol, and a light yellow solid substance (2.4 g, the yield: 82%) was obtained. The obtained product was identified to be 9-(4-chlorophenyl)-10-(4-(2,2-diphenylvinyl)phenyl)anthracene in accordance with $^1$H-NMR.

$^1$H-NMR (CDCl$_3$, TMS) δ: 7.14 (1H, s), 7.2-7.4 (20H, m), 7.5-7.7 (6H, m).

(4) Synthesis of 9-(4-diphenylaminophenyl)-10-(4-(2,2-diphenylvinyl)phenyl)anthracene (Synthesis of Compound (A5))

Under an atmosphere of argon, 9-(4-chlorophenyl)-10-(4-(2,2-diphenylvinyl)phenyl)anthracene (2.4 g, 4.4 mmole), diphenylamine (0.9 g, 5.3 mmole, 1.2 eq), tris(dibenzylideneacetone)dipalladium(0) (0.1 g, 0.11 mmole, 5% Pd), a toluene solution of tri-t-butylphosphine (66% by weight, 0.05 ml, 0.16 mmole, 0.7 eq to Pd) and sodium t-butoxide (0.6 g, 6.3 mmole, 1.4 eq) were suspended in anhydrous toluene (20 ml). The resultant suspension was refluxed for 8 hours. The reaction mixture was filtered and washed with toluene, water and methanol, and a green solid substance was obtained. The obtained solid substance was suspended in boiling toluene (40 ml). After the suspension was cooled while being left standing, the suspension was filtered, and a green solid substance (2.4 g, 81%) was obtained. The result of examination of the obtained product in accordance with $^1$H-NMR was as follows:

$^1$H-NMR (CDCl$_3$, TMS) δ: 7.0-7.4 (33H, m), 7.6-7.9 (4H, m).

The obtained solid substance (2.4 g) was purified by sublimation at 360° C./10$^{-6}$ Torr for 1 hour, and a light yellow solid substance (1.9 g) was obtained. It was confirmed in accordance with FDMS that the obtained product was the object compound (Compound (A5)). The results of measurements of Eg, Ip and Tg are also shown in the following.

FDMS: calcd. for C$_{52}$H$_{37}$=675, found m/z=675 (M+, 100)
λmax: 398, 379, 360, 307 nm (PhMe)
Fmax: 457 nm (PhMe: λex=398 nm)
Ip=5.73 eV (200 nW, 16 Y/eV)
Tg=114° C.

SYNTHESIS EXAMPLE 6

Synthesis of Compound (A11))

Synthesis of 9-(4-diphenylaminophenyl)-10-(3,4-diphenylphenyl)anthracene (Compound (A11))

Under an atmosphere of argon, 9-(4-chlorophenyl)-10-(3,4-diphenylphenyl)anthracene (2.3 g, 4.4 mmole), diphenylamine (0.9 g, 5.3 mmole, 1.2 eq), tris(dibenzylideneacetone)dipalladium(0) (0.1 g, 0.11 mmole, 5% Pd), a toluene solution of tri-t-butylphosphine (66% by weight, 0.05 ml, 0.16 mmole, 0.7 eq to Pd) and sodium t-butoxide (0.6 g, 6.3 mmole, 1.4 eq) were suspended in anhydrous toluene (20 ml). The resultant mixture was refluxed for 8 hours. The reaction mixture was filtered and washed with toluene, water and methanol, and a light yellow solid substance was obtained. The obtained solid substance was suspended in boiling toluene (40 ml). After the suspension was cooled while being left standing, the suspension was filtered, and a light yellow solid substance (2.2 g, the yield: 78%) was obtained. It was confirmed in accordance with $^1$H-NMR and FDMS that the obtained product was Compound (A11).

SYNTHESIS EXAMPLE 7

Synthesis of Compound (A14)

Synthesis of 9-(4-diphenylaminophenyl)-10-(3,5-diphenylphenyl)anthracene (Compound (A14))

Under an atmosphere of argon, 9-(4-chlorophenyl)-10-(3,5-diphenylphenyl)anthracene (2.3 g, 4.4 mmole), diphenylamine (0.9 g, 5.3 mmole, 1.2 eq), tris(dibenzylideneacetone)dipalladium(0) (0.1 g, 0.11 mmole, 5% Pd), a toluene solution of tri-t-butylphosphine (66% by weight, 0.05 ml, 0.16 mmole, 0.7 eq to Pd) and sodium t-butoxide (0.6 g, 6.3 mmole, 1.4 eq) were suspended in anhydrous toluene (20 ml). The resultant mixture was refluxed for 8 hours. The reaction mixture was filtered and washed with toluene, water and methanol, and a light yellow solid substance was obtained. The obtained solid substance was suspended in boiling toluene (40 ml). After the suspension was cooled while being left standing, the suspension was filtered, and a light yellow solid substance (2.5 g, the yield: 86%) was obtained. It was confirmed in accordance with $^1$H-NMR and FDMS that the obtained product was Compound (A14).

SYNTHESIS EXAMPLE 8

Synthesis of Compound (A20)

Synthesis of 9-(9,9-didimethylfluoren-2-yl)-10-(4-(2,2-diphenylvinyl)phenyl)anthracene (Compound (A20))

Under an atmosphere of argon, 9-(9,9-dimethylfluoren-2-yl)-10-bromoanthracene (2.8 g, 6.2 mmole), 4-(2,2-diphenylvinyl)phenylboric acid (2.0 g, 6.7 mmole, 1.1 eq) and tetrakis(triphenylphosphine)palladium(0) (0.14 g, 0.12 mmole, 2% Pd) were suspended in toluene (20 ml). To the obtained suspension, a 2M aqueous solution of sodium carbonate (2.1 g, 20 mmole, 3 eq/10 ml) was added, and the resultant mixture was refluxed for 10 hours. The reaction mixture was filtered and washed with water and methanol, and a light yellow solid substance was obtained. The obtained solid substance was suspended in boiling toluene (30 ml). After the suspension was cooled while being left standing, the suspension was filtered, and a light yellow solid substance (3.0 g, the yield: 78%) was obtained. It was confirmed in accordance with $^1$H-NMR and FDMS that the obtained product was Compound (A20).

EXAMPLE 1

A glass substrate (manufactured by GEOMATEC Company) of 25 mm×75 mm×1.1 mm (thickness) having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of N,N'-bis(N,N'-diphenyl-4-aminophenyl)-N,N-β-naphthyl-4,4'-diamino-1,1'-biphenyl (a film of TPD232) having a thickness of 60 nm was formed in a manner such that the formed film covered the transparent electrode. The formed film of TPD232 worked as the hole injecting layer. On the formed film of TPD232, a film of N,N,N',N'-tetrakis(4-biphenyl)-4,4'-benzidine (a film of BPTPD) having a thickness of 20 nm was formed. The formed film of BPTPD worked as the hole transporting layer. On the formed film of BPTPD, a film of the above Compound (A1) having a thickness of 40 nm was formed by vapor deposition. The formed film of Compound (A1) worked as the light emitting layer. On the film formed above, a film of Alq shown in the following having a thickness of 10 nm was formed. The film of Alq worked as the electron injecting layer. Thereafter, Li (the source of lithium: manufactured by SAES GETTERS Company) as the reducing dopant and Alq were binary vapor deposited, and an Alq:Li film (the thickness: 10 nm) was formed as the electron injecting layer (cathode). On the formed Alq:Li film, metallic aluminum was vapor deposited to form a metal cathode, and an organic EL device was prepared.

When a direct current voltage of 6 V was applied to the organic EL device prepared above, blue light was emitted at a luminance of 176 cd/m$^2$ and an efficiency of the light emission of 2.2 cd/A.

The device was then subjected to the evaluation by the storage test at a high temperature. Namely, after the above device was sealed, the device was left standing in a thermostatic oven kept at 100° C. for 500 hours, and it was examined whether defects such as changes in the bright spots and the color were found on the light emitting surface by observation using a stereomicroscope of a magnification of 200 times. The results are shown in Table 1.

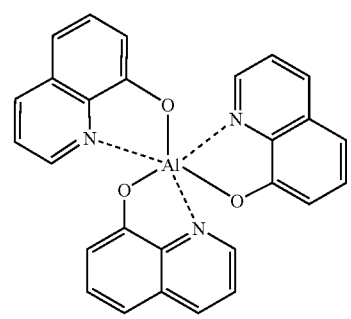

Alq

EXAMPLES 2 TO 10

Organic EL devices were prepared in accordance with the same procedures as those conducted in Example 1 except that compounds shown in Table 1 were used in place of Compound (A1) used in Example 1. The voltage applied to the devices, the luminance of emitted light, the efficiency of light emission and the color of emitted light of the devices, the glass transition temperature Tg of the used compound and the results of the storage test of the devices at a high temperature are shown in Table 1.

COMPARATIVE EXAMPLE 1

An organic EL device was prepared in accordance with the same procedures as those conducted in Example 1 except that Compound (C1) shown in the following, which is an arylanthracene compound described in the U.S. Pat. No. 5,935,721, was used in place of Compound (A1) used in Example 1. The voltage applied to the device, the luminance of emitted light, the efficiency of light emission and the color of emitted light of the devices, the glass transition temperature Tg of the used compound and the results of the storage test of the device at a high temperature are shown in Table 1.

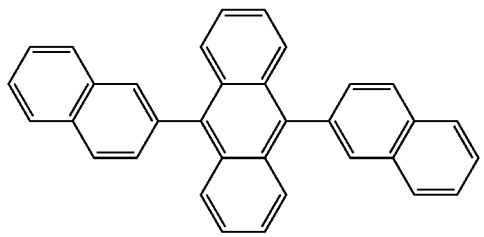

(C1)

COMPARATIVE EXAMPLE 2

An organic EL device was prepared in accordance with the same procedures as those conducted in Example 1 except that Compound (C2) shown in the following, which is an arylanthracene compound described in Japanese Patent Application Laid-Open No. 2000-273056, was used in place of Compound (A1) used in Example 1. The voltage applied to the device, the luminance of emitted light, the efficiency of light emission and the color of emitted light of the device, the glass transition temperature Tg of the used compound and the results of the storage test of the device at a high temperature are shown in Table 1.

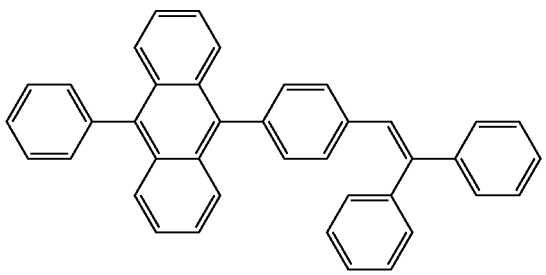

(C2)

COMPARATIVE EXAMPLE 3

An organic EL device was prepared in accordance with the same procedures as those conducted in Example 1 except that Compound (C3) shown in the following, which is another arylanthracene compound described in Japanese Patent Application Laid-Open No. 2000-273056, was used in place of Compound (A1) used in Example 1. The voltage applied to the device, the luminance of emitted light, the efficiency of light emission and the color of emitted light of the device, the glass transition temperature Tg of the used compound and the results of the storage test of the device at a high temperature are shown in Table 1.

TABLE 1

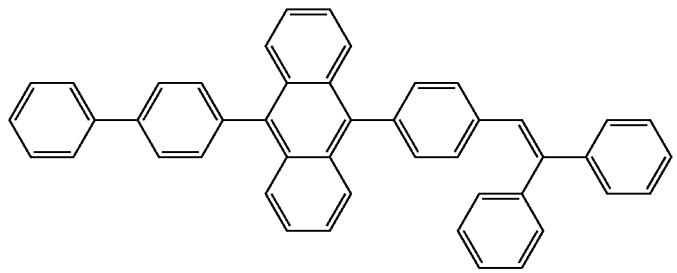

(C3)

| | Compound of light emitting layer | Voltage (V) | Luminance of emitted light (cd/m$^2$) | Efficiency of light emission (cd/A) | Color of emitted light | Tg of compound (° C.) | Storage test at high temperature |
|---|---|---|---|---|---|---|---|
| Example 1 | (A1) | 6.0 | 176 | 2.2 | blue | 108 | good |
| Example 2 | (A2) | 6.0 | 200 | 2.3 | blue | 120 | good |
| Example 3 | (A3) | 6.0 | 161 | 3.1 | blue | 122 | good |
| Example 4 | (A4) | 6.0 | 110 | 2.3 | blue | 115 | good |
| Example 5 | (A5) | 6.0 | 780 | 2.0 | blue | 114 | good |

TABLE 1-continued (C3)

[Chemical structure of compound C3]

| Compound of light emitting layer | Voltage (V) | Luminance of emitted light (cd/m²) | Efficiency of light emission (cd/A) | Color of emitted light | Tg of compound (° C.) | Storage test at high temperature |
|---|---|---|---|---|---|---|
| Example 6 | (A6) | 6.0 | 180 | 2.8 | bluish green | 112 | good |
| Example 7 | (A10) | 6.0 | 250 | 2.9 | blue | 128 | good |
| Example 8 | (A20) | 6.0 | 180 | 3.1 | blue | 124 | good |
| Example 9 | (B1) | 6.0 | 260 | 2.2 | blue | 156 | good |
| Example 10 | (B2) | 6.0 | 313 | 3.1 | blue | 152 | good |
| Comparative Example 1 | (C1) | 6.0 | 120 | 2.1 | bluish green | ND | crystallized |
| Comparative Example 2 | (C2) | 6.0 | 125 | 2.1 | blue | 95 | crystallized |
| Comparative Example 3 | (C3) | 6.0 | 153 | 2.5 | blue | 109 | crystallized |

*In the test of storage at a high temperature, the result was evaluated as "good" when no defects such as changes in the bright spots and the color on the light emitting surface were found, and as "crystallized" when defects such as changes in the bright spots and the color on the light emitting surface were found. In the column of Tg, ND means that no Tg was observed in the measurement in accordance with the differential scanning calorimetry (DSC).

As shown in Table 1, in Comparative Example 1 in which Compound (C1) having an excellentd symmetry was used, defects appeared on the light emitting surface due to crystallization, and the emitted light was bluish green, i.e., the purity of the blue color was not excellent. In Comparative Examples 2 and 3, crystallization took place even though Compounds (C2) and (C3) had asymmetric molecular structure in the horizontal direction. This is considered to have taken place due to low glass transition temperatures. Since the compounds of the present invention were asymmetric and had relatively high glass transition temperatures, the results of the storage test at a high temperature were excellent.

EXAMPLE 11

A glass substrate (manufactured by GEOMATEC Company) of 25 mm×75 mm×1.1 mm (thickness) having an ITO transparent electrode was cleaned by application of ultrasonic wave in isopropyl alcohol for 5 minutes and then by exposure to ozone generated by ultraviolet light for 30 minutes. The glass substrate having the transparent electrode lines which had been cleaned was attached to a substrate holder of a vacuum vapor deposition apparatus. On the surface of the cleaned substrate at the side having the transparent electrode, a film of TPD232 having a thickness of 60 nm was formed in a manner such that the formed film covered the transparent electrode. The formed film of TPD232 worked as the hole injecting layer. On the formed film of TPD232, a film of BPTPD having a thickness of 20 nm was formed. The formed film of BPTPD worked as the hole transporting layer. On the formed film of BPTPD, a film of the above Compound (A1) having a thickness of 40 nm was formed by vapor deposition. The formed film of Compound (A1) worked as the light emitting layer. At the same time, a styrylamine-based light emitting molecule (D1) shown in the following was added in an amount of 7% by weight. On the film formed above, a film of Alq having a thickness of 20 nm was formed. The film of Alq worked as the electron injecting layer. Thereafter, Li (the source of lithium: manufactured by SAES GETTERS Company) as the reducing dopant and Alq were binary vapor deposited, and an Alq:Li film (the thickness: 10 nm) was formed as the electron injecting layer (cathode). On the formed Alq:Li film, metallic aluminum was vapor deposited to form a metal cathode, and an organic EL device was prepared.

When a direct current voltage of 5.5 V was applied to the organic EL device prepared above, blue light was emitted at a luminance of 200 cd/m² and an efficiency of the light emission of 5.5 cd/A. When the device was driven at an initial luminance of 500 cd/m² under a constant electric current, the time before the luminance decreased to a half of the initial value (the half life) was 3,000 hours.

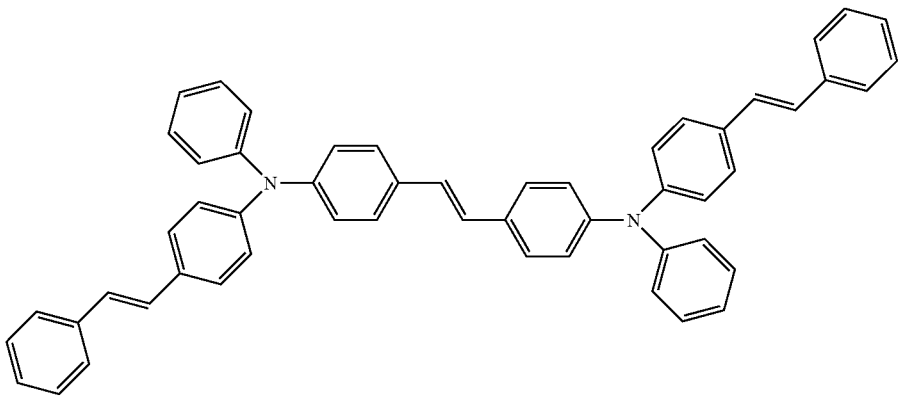

COMPARATIVE EXAMPLE 4

An organic EL device was prepared in accordance with the same procedures as those conducted in Example 1 except that Compound (C1) shown in the above, which is an arylanthracene compound described in the U.S. Pat. No. 5,935,721, was used in place of Compound (A1) used in Example 1. The voltage applied to the device, the luminance of emitted light, the efficiency of light emission and the color of emitted light of the device, the glass transition temperature Tg of the used compound and the results of the storage test of the device at a high temperature are shown in Table 1.

When a direct current voltage of 5.5 V was applied to the organic EL device prepared above, blue light was emitted at a luminance of 180 cd/m² and an efficiency of the light emission of 5.0 cd/A. When the device was driven at an initial luminance of 500 cd/m² under a constant electric current, the time before the luminance decreased to a half of the initial value (the half life) was as short as 1,500 hours.

INDUSTRIAL APPLICABILITY

As described in detail in the above, the organic EL device which exhibits a great luminance of emitted light, a great efficiency of light emission and a high purity of color, emits bluish light, is excellent in stability at high temperatures and has a long life can be obtained by utilizing the novel aromatic compound of the present invention. Therefore, the organic EL device of the present invention is very useful as the light source for various electronic instruments.

The invention claimed is:

1. An aromatic compound having an asymmetric molecular structure which is represented by the following general formula (I):

wherein A and B are not the same, Ar represents a substituted or unsubstituted anthracendiyl group, B represents a substituted aryl group having 6 to 60 carbon atoms, or a heterocyclic group which has 2 to 60 carbon atoms, wherein the aryl group or heterocyclic group is mono-substituted with an alkenyl group or an arylamino group, A represents a group which is selected from groups represented by the following general formulae (1), (2), and (9):

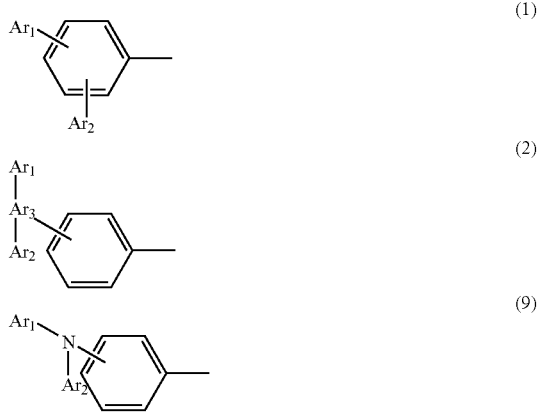

wherein $Ar_1$ and $Ar_2$ each independently represents an aryl group having 6 to 30 carbon atoms, $Ar_5$ represents a trivalent aeomatic residue group having 6 to 30 carbon atoms, the foregoing general formulae (1), (2), and (9) may be substituted with substituted or unsubstituted alkyl groups having 1 to 30 carbon atoms or a substituted or unsubstituted phenyl group; and A does not represent phenyl group substituted with an arylamino group when the group represented by B is substituted with an arylamino group.

2. The aromatic compound according to claim 1, wherein B in the general formula (I) represents a heterocyclic group which has 2 to 60 carbon atoms and is mono-substituted with an alkenyl group or an arylamino group or an aryl group which has 6 to 60 carbon atoms and is mono-substituted with an alkenyl group or an arylamino group.

3. An aromatic compound having an asymmetric molecular structure which is represented by the following general formula (II):

wherein A' and B are not the same, Ar represents a substituted or unsubstituted anthracendiyl group, B represents a substituted aryl group having 6 to 60 carbon atoms, or a heterocyclic group which has 2 to 60 carbon atoms, wherein the aryl group or heterocyclic group is mono-substituted with an alkenyl group or an arylamino group, A' represents a group which is selected from groups represented by the following general formulae (2), (9), (11) and (12):

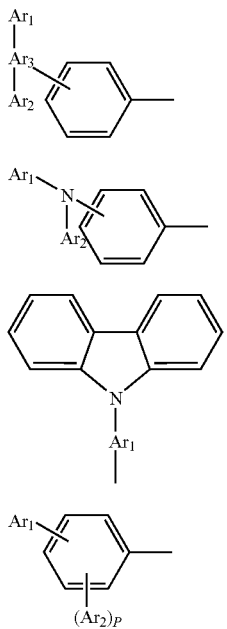

wherein $Ar_1$ and $Ar_2$ each independently represents an aryl group having 6 to 30 carbon atoms, $Ar_4$ represents an arylene group having 6 to 30 carbon atoms, $Ar_5$ represents a trivalent aromatic residue group having 6 to 30 carbon atoms, and p in the general formula (12) represents 0 or 1;

the foregoing general formulae (2), (9), (11) and (12) may be substituted with substituted or unsubstituted alkyl groups having 1 to 30 carbon atoms or a substituted or unsubstituted phenyl group; and A' does not represent phenyl group substituted with an arylamino group when the group represented by B is substituted with an arylamino group.

4. The aromatic compound according to claim 3, wherein B in the general formula (II) represents a heterocyclic group which has 2 to 60 carbon atoms and is mono-substituted with an alkenyl group or an arylamino group or an aryl group which has 6 to 60 carbon atoms and is mono-substituted with an alkenyl group or an arylamino group.

5. The aromatic compound according to any one of claims 1 to 4, which is a material for organic electroluminescence devices.

6. An organic electroluminescence device which comprises a cathode, an anode and an organic thin film layer comprising at least one layer containing a light emitting layer and sandwiched between the cathode and the anode, wherein at least one layer in the organic thin film layer comprises a novel aromatic compound described in any one of claims 1 to 4 singly or as a component of a mixture.

7. An organic electroluminescence device which comprises a cathode, an anode and an organic thin film layer comprising at least one layer containing a light emitting layer and sandwiched between the cathode and the anode, wherein the organic thin film layer comprises at least one of an electron transporting layer and a hole transporting layer, and at least one of the electron transporting layer and the hole transporting layer comprises a novel aromatic compound described in any one of claims 1 to 4 singly or as a component of a mixture.

8. The organic electroluminescence device according to claim 6, wherein the light emitting layer further comprises an arylamine compound.

9. The organic electroluminescence device according to claim 6, wherein the light emitting layer further comprises a styrylamine compound.

10. The organic electroluminescence device according to claim 6, wherein an electron transporting region or an interface region between the cathode and the organic thin film layer comprises a reducing dopant.

11. The organic electroluminescence device according to claim 6, which emits bluish light.

* * * * *